US 9,271,632 B2

(12) United States Patent
Naito

(10) Patent No.: US 9,271,632 B2
(45) Date of Patent: Mar. 1, 2016

(54) ROTATION UNIT, INSERTION APPARATUS, INSERTION BODY, AND INSERTION SYSTEM

(71) Applicant: OLYMPUS MEDICAL SYSTEMS CORP., Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/268,118

(22) Filed: May 2, 2014

(65) Prior Publication Data
US 2014/0323805 A1    Oct. 30, 2014

Related U.S. Application Data

(63) Continuation of application No. PCT/JP2013/074597, filed on Sep. 11, 2013.

(30) Foreign Application Priority Data

Sep. 27, 2012  (JP) ................................. 2012-214068
Sep. 27, 2012  (JP) ................................. 2012-214069

(51) Int. Cl.
*A61B 1/04* (2006.01)
*A61B 1/00* (2006.01)

(52) U.S. Cl.
CPC ........... *A61B 1/00071* (2013.01); *A61B 1/0016* (2013.01); *A61B 1/00073* (2013.01); *A61B 1/00135* (2013.01)

(58) Field of Classification Search
USPC ......... 600/114–115, 117–118, 121–123, 137; 604/108, 165.04
See application file for complete search history.

(56) References Cited

U.S. PATENT DOCUMENTS 4,998,282  A  *  3/1991  Shishido et al. ................. 381/77
5,415,634  A  *  5/1995  Glynn et al. ............. 604/103.08
(Continued)

FOREIGN PATENT DOCUMENTS

JP    2005-288035 A    10/2005
JP    2005-319121 A    11/2005
(Continued)

OTHER PUBLICATIONS

International Search Report dated Nov. 26, 2013 issued in PCT/JP2013/074597.

(Continued)

*Primary Examiner* — Matthew J Kasztejna
(74) *Attorney, Agent, or Firm* — Scully, Scott, Murphy & Presser, PC

(57) ABSTRACT

A cylindrical rotation unit attachable to an elongated insertion unit which includes a base in which a central axis is defined, and a rotation member provided on an outer circumference of the base movably in an axial direction of the central axis relative to the base and rotatably around the central axis in response to the rotation of a rotation force transmission portion which is rotatable around a longitudinal axis parallel with the central axis of the base includes: an engagement portion attachable to and detachable from an outer circumferential surface of the base; and a contact portion which is provided to contact on the rotation member away from the engagement portion and which disposes the rotation member on an outer circumference of the rotation force transmission portion while the engagement portion is engaged with the outer circumferential surface of the base.

20 Claims, 16 Drawing Sheets

(56) References Cited

U.S. PATENT DOCUMENTS

| | | | |
|---|---|---|---|
| 7,621,867 B2* | 11/2009 | Kura et al. | 600/137 |
| 7,862,504 B2* | 1/2011 | Kura et al. | 600/114 |
| 8,277,374 B2* | 10/2012 | Tsumaru et al. | 600/115 |
| 8,574,220 B2* | 11/2013 | Frassica et al. | 604/528 |
| 8,747,300 B2* | 6/2014 | Frassica et al. | 600/112 |
| 2005/0272976 A1* | 12/2005 | Tanaka et al. | 600/114 |
| 2008/0262305 A1* | 10/2008 | Omoto | 600/118 |
| 2009/0012359 A1* | 1/2009 | Tanaka et al. | 600/114 |
| 2009/0209812 A1* | 8/2009 | Omoto | 600/110 |
| 2009/0281384 A1* | 11/2009 | Tsumaru et al. | 600/114 |

FOREIGN PATENT DOCUMENTS

| | | |
|---|---|---|
| JP | 2005-329000 A | 12/2005 |
| WO | WO 2011140118 A1 | 11/2011 |

OTHER PUBLICATIONS

English translation of International Preliminary Report on Patentability dated Apr. 9, 2015 together with the Written Opinion received in related International Application No. PCT/JP2013/074597.

* cited by examiner

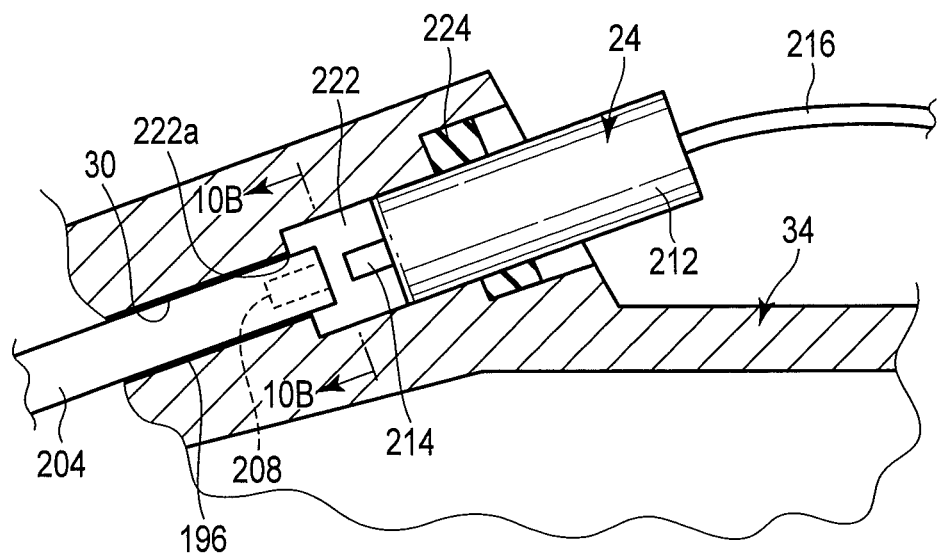
F I G. 10A
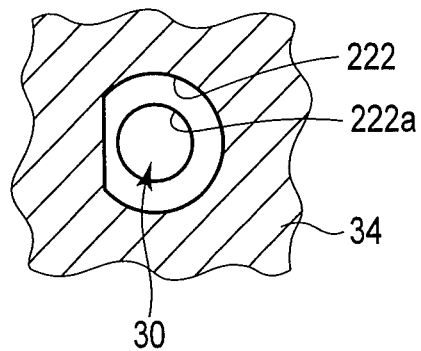
F I G. 10B

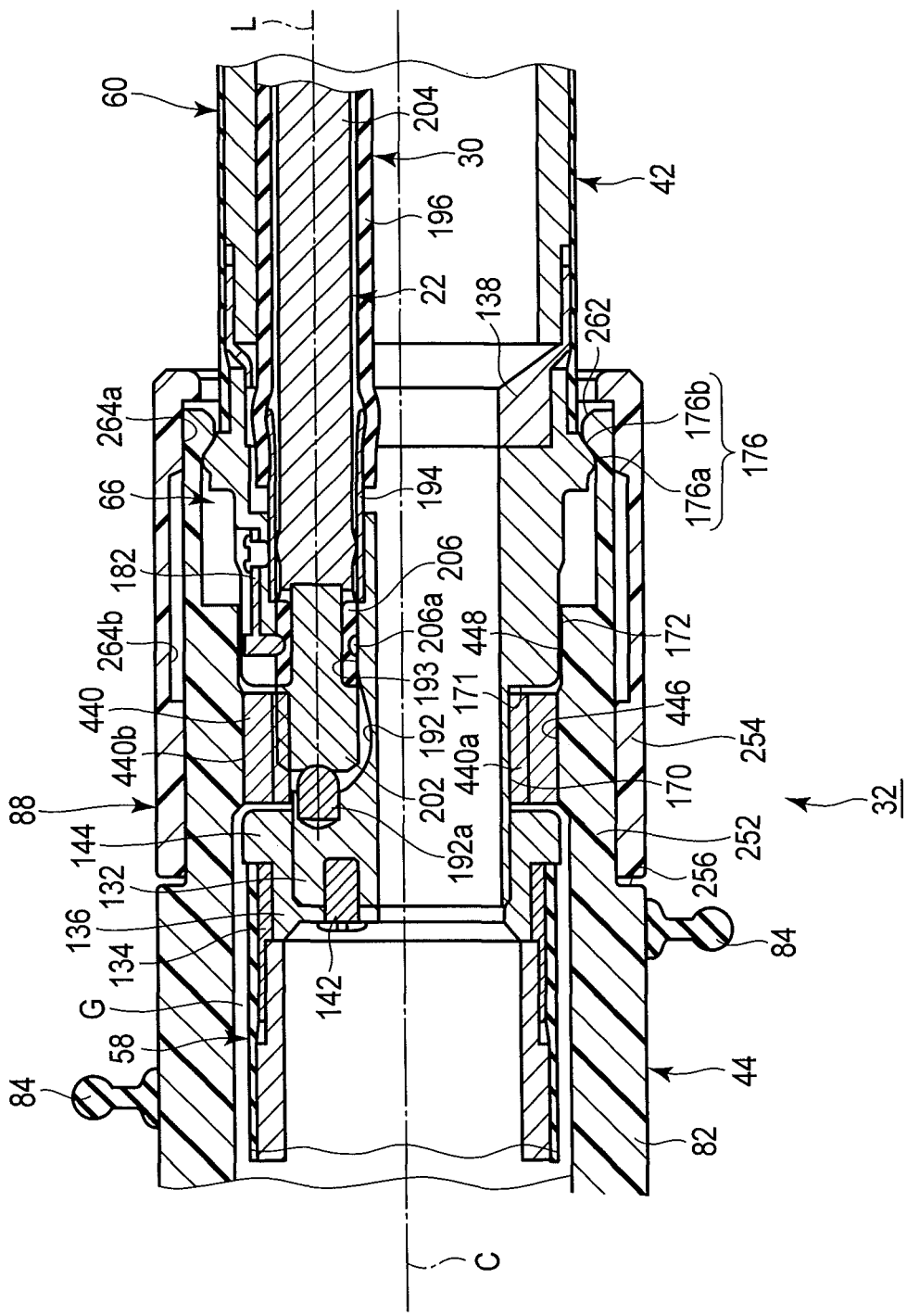
F I G. 16

ROTATION UNIT, INSERTION APPARATUS, INSERTION BODY, AND INSERTION SYSTEM

CROSS-REFERENCE TO RELATED APPLICATIONS

This application is a Continuation Application of PCT Application No. PCT/JP2013/074597, filed Sep. 11, 2013 and based upon and claiming the benefit of priority from prior Japanese Patent Application No. 2012-214068 and prior Japanese Patent Application No. 2012-214069, filed Sep. 27, 2012, the entire contents of all of which are incorporated herein by reference.

BACKGROUND OF THE INVENTION

1. Field of the Invention

This invention relates to a rotation unit attachable to an insertion unit insertable into a small hole, an insertion apparatus, an insertion body, an insertion apparatus in which this insertion body is provided, and an insertion system including the insertion body and the insertion apparatus.

2. Description of the Related Art

For example, Jpn. Pat. Appln. KOKAI Publication No. 2005-329000 has disclosed a structure in which a rotation unit having a fin portion outside the distal end of an insertion portion of an endoscope and having a permanent magnet inside can be rotated if a magnetic force is applied to the rotation unit from the outside of the rotation unit. The rotation unit is provided outside a slide pipe which has a flange at the proximal end to support the end of the rotation unit. A thread portion is formed at the end of the slide pipe, and a fixing ring member is threaded into the thread portion so that the rotation unit is fixed and does not come off the slide pipe.

BRIEF SUMMARY OF THE INVENTION

According to one embodiment of the present invention, a cylindrical rotation unit attachable to an elongated insertion unit which includes a base in which a central axis is defined, and a rotation member provided on an outer circumference of the base movably in an axial direction of the central axis relative to the base and rotatably around the central axis in response to the rotation of a rotation force transmission portion which is rotatable around a longitudinal axis parallel with the central axis of the base, includes: an engagement portion attachable to and detachable from an outer circumferential surface of the base; and a contact portion which is provided to contact on the rotation member away from the engagement portion and which disposes the rotation member on an outer circumference of the rotation force transmission portion while the engagement portion is engaged with the outer circumferential surface of the base.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10A is a schematic longitudinal sectional view showing how a rotation shaft of a driving source is to be connected to the proximal end of a drive shaft projecting toward the proximal side relative to an exit where the rotation force transmission unit is inserted through an insertion unit, in the insertion portion of the endoscope of the endoscope system according to the first embodiment;

FIG. 10B is a schematic cross sectional view of a position taken along the arrow line 10B-10B in FIG. 10A;

FIG. 16 is a schematic longitudinal sectional view showing how the rotation unit of the insertion portion of the endoscope of the endoscope system according to the fourth modification of the first and second embodiments is attached to the outer circumference of the insertion unit.

DETAILED DESCRIPTION OF THE INVENTION

Embodiments of this invention will be described hereinafter with reference to the drawings.

The first embodiment is described with reference to FIG. 1 to FIG. 10B.

Figure 1:
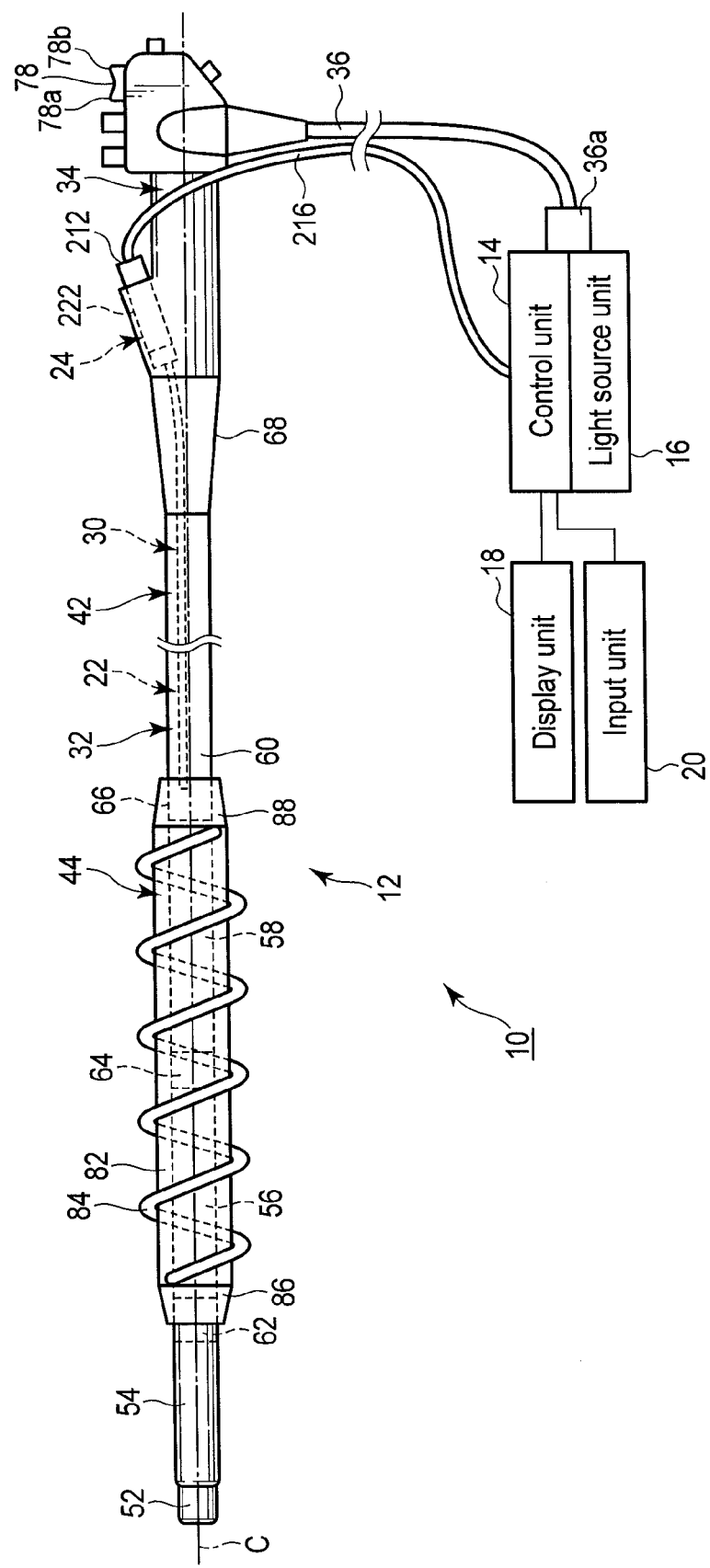
FIG. 1 is a schematic diagram showing an endoscope system according to first and second embodiments of the present invention.

As shown in FIG. 1, an endoscope system 10 according to this embodiment has an endoscope (insertion apparatus) 12, a control unit 14 which includes an unshown image processing unit such as an image processor and which controls the whole endoscope system 10, a light source unit 16, a display unit 18 such as a monitor, and an input unit 20 such as a keyboard and a mouse.

The light source unit 16 is electrically connected to the control unit 14. The display unit 18 and the input unit 20 are electrically connected to the control unit 14. When a light source is provided in a distal hard portion 52 of a later-described insertion portion 32 of the endoscope 12, the light source unit 16 is unnecessary.

In the endoscope system 10 according to this embodiment, a rotation force transmission unit (insertion body) 22 shown in FIG. 2A and a driving source 24 shown in FIG. 1 can be attached to and detached from the endoscope 12 from the side of a later-described operation portion 34. That is, the endoscope 12 has a channel 30 which defines an insertion channel to attach and detach the rotation force transmission unit 22 and the driving source 24. The channel 30 then defines a longitudinal axis L on which the rotation force transmission unit 22 is inserted at a position which is out of alignment with a later-described central axis C.

The endoscope 12 includes the insertion portion 32 to be inserted into a narrow hole such as a lumen, and the operation portion 34 provided at the proximal end of the insertion portion 32. The insertion portion 32 is inserted into a lumen such as the inside of a large intestine or the inside of a small intestine. One end of a universal cable 36 is connected to the operation portion 34. A scope connector 36a is provided at the other end of the universal cable 36. The scope connector 36a is connected to the control unit 14 and the light source unit 16.

The insertion portion 32 includes an elongated insertion unit 42, and a cylindrical rotation unit 44 which is detachably attached to the outer circumference (outside) of the insertion unit 42 and which is rotatable around the later-described central axis C of the insertion unit 42.

The insertion unit 42 has, in order from the distal end to the proximal end, the distal hard portion 52, an active bending portion 54, a passive bending portion 56 which passively bends in response to the application of an external force, a first flexible tube 58, and a second flexible tube 60. The central axis C of the insertion portion 32 is defined by the distal end of the insertion unit 42 (the distal end of the distal hard portion 52) and the proximal end thereof (the proximal end of the second flexible tube 60).

The active bending portion 54 and the passive bending portion 56 are connected to each other by a bending tube connection portion 62. The passive bending portion 56 and the first flexible tube 58 are connected to each other by an intermediary connection portion 64. The first flexible tube 58 and the second flexible tube 60 are connected to each other by a flexible tube connection portion 66. A break prevention 68 is provided between the second flexible tube 60 and the operation portion 34. That is, the insertion unit 42 has the bending tube connection portion 62, the intermediary connection portion 64, and the flexible tube connection portion 66, in addition to the distal hard portion 52, the active bending portion 54, the passive bending portion 56, the first flexible tube 58, and the second flexible tube 60.

The distal ends of various extensive components 12a extended inside the endoscope 12 such as an observation optical system, an illumination optical system, and a treatment instrument channel are fixed to the distal hard portion 52 shown in FIG. 1. The extensive components 12a of the observation optical system and the illumination optical system are respectively connected to the connector 36a through the insertion unit 42, the operation portion 34, and the universal cable 36. The extensive component 12a, that is, a channel tube of the treatment instrument channel is connected to the operation portion 34 through the insertion unit 42.

Figure 3:
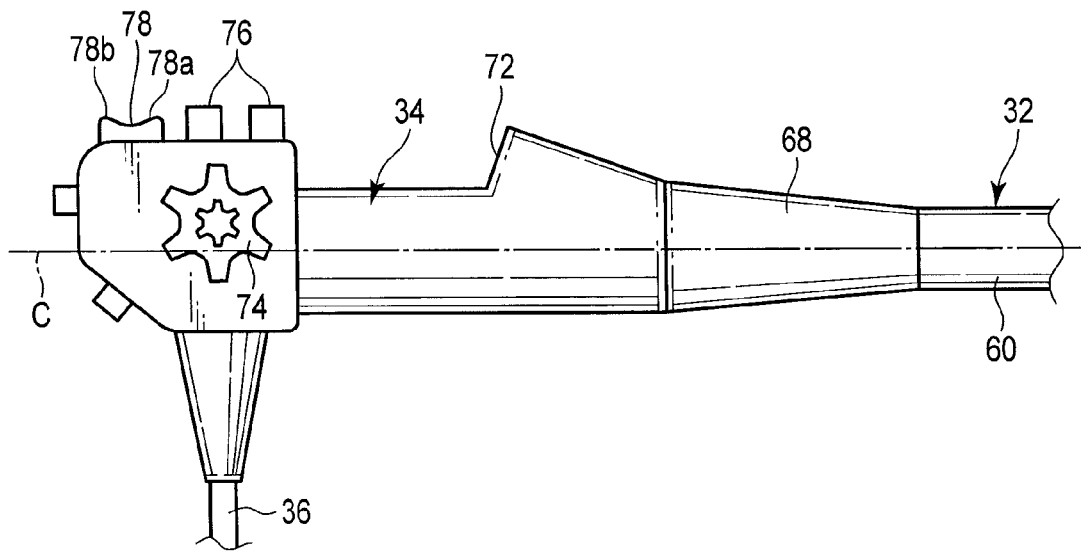
FIG. 3 is a schematic diagram showing an operation portion of the endoscope of the endoscope system according to the first embodiment when viewed from the rear side in FIG. 1.

FIG. 3 shows the opposite side surface of the operation portion 34 shown in FIG. 1. As shown in FIG. 3, the operation portion 34 has a treatment instrument insertion opening 72 to which the proximal end of the extensive component 12a of the treatment instrument channel is connected. Therefore, a treatment instrument inserted from the treatment instrument insertion opening 72 projects from the distal end of the distal hard portion 52 through the extensive component 12a, that is, the treatment instrument channel.

Although described later, the operation portion 34 has an attachment portion 222 (see FIG. 10A) which is provided to be parallel with the treatment instrument insertion opening 72 and which the driving source 24 can be attached to and detached from.

As shown in FIG. 3, a bending operation knob 74 serving as a bending operation input portion to which a bending operation of the active bending portion 54 is input is provided on the outer surface of the operation portion 34. Inside the operation portion 34, the proximal end of an unshown bending wire for bending the active bending portion 54 is connected to the bending operation knob 74. The bending wire extends inside the insertion unit 42 (insertion portion 32) along the central axis C, and has its distal end connected to the distal end of the active bending portion 54. In response to the bending operation in the bending operation knob 74, the active bending portion 54 is curved by the pulling of the bending wire. The passive bending portion 56 is passively bent by direct application of an external force or by indirect application of an external force via the active bending portion 54. For example, if an external force in a direction perpendicular to the central axis C is applied to the passive bending portion 56, the passive bending portion 56 is bent. If an external force in a direction perpendicular to the central axis C is applied to the bent active bending portion 54, the external force is also applied to the passive bending portion 56 via the active bending portion 54, and the passive bending portion 56 is bent.

The operation portion 34 is provided with various switches 76 such as an air/water supply switch and a suction switch. The operation portion 34 is also provided with a rotational operation input switch 78 which outputs, to the control unit 14, a signal to relatively rotate the rotation unit 44 around the central axis C of the insertion unit 42. For example, if a position indicated by the sign 78a is pressed to incline the rotational operation input switch 78, the rotational operation input switch 78 outputs, to the control unit 14, a signal to rotate the rotation unit 44 in a first direction. If a position indicated by the sign 78b is pressed to incline the rotational operation input switch 78, the rotational operation input switch 78 outputs, to the control unit 14, a signal to rotate the rotation unit 44 in a second direction opposite to the first direction.

The rotation unit 44 on the outer circumference of the insertion unit 42 includes a tube body 82 extending along the central axis C, a fin portion 84 extending spirally relative to the central axis C on the outer circumferential portion of the tube body 82, a tube distal portion 86 provided at the distal end of the tube body 82, and a tube proximal portion (cylindrical portion) 88 provided at the proximal end of the tube body 82. The tube body 82, the fin portion 84, the tube distal portion 86, and the tube proximal portion 88 can be disposed outside the insertion unit 42, and are rotatable around the central axis C and movable along the axial direction of the central axis C.

Figure 4:
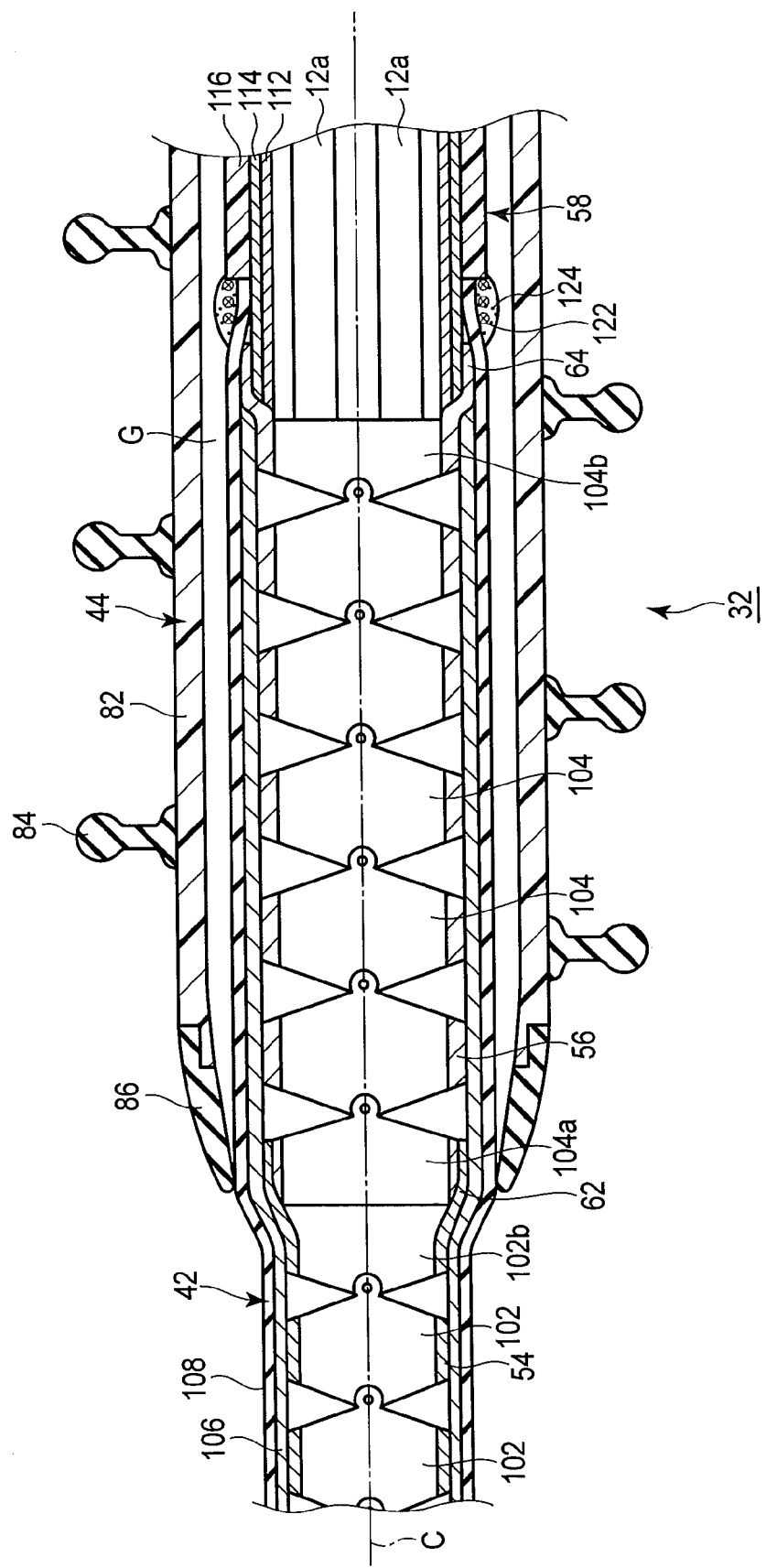
FIG. 4 is a schematic longitudinal sectional view showing part of an active bending portion, a passive bending portion, and part of a first flexible tube in an insertion portion of the endoscope of the endoscope system according to the first embodiment.

The configurations of the insertion unit 42 and the rotation unit 44 in the vicinity of the passive bending portion 56 are shown in FIG. 4. The configurations of the insertion unit 42 and the rotation unit 44 in the vicinity of the flexible tube connection portion 66 are shown in FIG. 5 to FIG. 9.

As shown in FIG. 4, the active bending portion 54 has metallic first bending rings 102. Each of the first bending rings 102 is pivotally coupled to the adjacent first bending ring 102. The distal end of the above-mentioned unshown bending wire is fixed to an unshown first bending ring located on the most distal direction side. When the bending wire is pulled, the first bending ring 102 pivots relative to the adjacent first bending ring 102, and the active bending portion 54 is bent.

The passive bending portion 56 has metallic second bending rings 104. Each of the second bending rings 104 is pivotally coupled to the adjacent second bending ring 104. No wire guide to support the bending wire is provided in each of the second bending rings 104. Therefore, in response to an external force applied in the direction perpendicular to the central axis C, the second bending ring 104 pivots relative to the adjacent second bending ring 104, and the passive bending portion 56 is bent.

A first bending ring 102b located on the most proximal direction side is fixed in a fit state to a second bending ring 104a located on the most distal direction side. The first bending ring 102b is fixed to the second bending ring 104a so that the bent tube connection portion 62 is formed between the active bending portion 54 and the passive bending portion 56. In the bent tube connection portion 62, the first bending ring 102b is fixed to the second bending ring 104a, and the thickness of a metallic portion formed by the first bending ring 102b and the second bending ring 104a is larger. Therefore, the bent tube connection portion 62 is less flexible than the active bending portion 54 and the passive bending portion 56, and is therefore not bent by the external force applied in the direction perpendicular to the central axis C.

The outer circumferences of the first bending rings 102 and the second bending rings 104 are covered with a metallic braided tube (braid) 106. The outer circumference of the braided tube 106 is covered with an outer tube 108. The bending portion outer tube 108 is made of, for example, fluoro rubber.

As shown in FIG. 4, the first flexible tube 58 is provided with a metallic first spiral tube (first flex) 112. The outer circumference of the first spiral tube 112 is covered with a metallic first braided tube (first braid) 114. The outer circumference of the first braided tube 114 is covered with a first outer tube 116. The first outer tube 116 is made of a material lower in flexibility than the outer tube 108 of the active bending portion 54 and the passive bending portion 56, such as a mixed resin material of polyurethane and polyester. When an external force is applied, the first spiral tube 112 becomes lower in bending performance than a coupler of the first bending rings 102 and a coupler of the second bending rings 104. Therefore, the first flexible tube 58 becomes lower in flexibility than the active bending portion 54 and the passive bending portion 56. However, the first flexible tube 58 is provided to have such a degree of flexibility that the first flexible tube 58 is bent by the external force applied in the direction perpendicular to the central axis C.

A second bending ring 104b located on the most proximal direction side is fixed in a fit state to the first spiral tube 112 and the first braided tube 114. The second bending ring 104b is fixed to the first spiral tube 112 and the first braided tube 114 so that the intermediary connection portion 64 is formed between the passive bending portion 56 and the first flexible tube 58. In the intermediary connection portion 64, the second bending ring 104b is fixed to the first spiral tube 112 and the first braided tube 114, and the thickness of a metallic portion formed by the second bending ring 104b, the first spiral tube 112, and the first braided tube 114 is larger. Therefore, the intermediary connection portion 64 is less flexible than the passive bending portion 56 and the first flexible tube 58, and is not bent by the external force applied in the direction perpendicular to the central axis C.

The proximal end of the bending portion outer tube 108 and the distal end of the first outer tube 116 are located in the intermediary connection portion 64. Between the bending portion outer tube 108 and the first outer tube 116, the first outer tube 116 and the bending portion outer tube 108 are wound with a thread 122, and are covered with an adhesive agent 124.

Although partly unshown, the extensive components 12a are inserted through the spaces inside the first bending rings 102, the bending tube connection portion 62, the second bending rings 104, the intermediary connection portion 64, and the first spiral tube 112.

The second flexible tube 60 shown in FIG. 5 to FIG. 9 is similar in configuration to the first flexible tube 58. Therefore, although not described in detail, the second flexible tube 60 is provided to have such a degree of flexibility that the second flexible tube 60 is curved by the external force applied in the direction perpendicular to the central axis C. A tubular member indicated by the sign 128a FIG. 5 to FIG. 8B represents a spiral tube and a braided tube provided on the outer circumference of the spiral tube. A circular member indicated by the sign 128b is used as an envelope. Therefore, the first flexible tube 58 and the second flexible tube 60 have the same configuration.

As shown in FIG. 5 to FIG. 9, the flexible tube connection portion 66 between the first flexible tube 58 and the second flexible tube 60 has a connection sleeve 132 made of, for example, a metallic material or a hard resin material to be a base, a first distal side sleeve 134, a second distal side sleeve 136, a proximal side sleeve 138, and a ring-shaped rotation member 140 having internal teeth (inner circumferential gear portion) 140a. The central axis C of The connection sleeve 132 is defined by the insertion unit 42.

The first and second distal side sleeves 134 and 136 have spaces 134a and 136a through which the extensive components 12a (see FIG. 4) that are not shown here are inserted. Similarly, the connection sleeve 132 has a cavity 132a through which the extensive components 12a (see FIG. 4) that are not shown here are inserted and which is in communication with the cavities 134a and 136a of the first and second distal side sleeves 134 and 136.

The first distal side sleeve 134 is provided at the proximal end of the first flexible tube 58. The second distal side sleeve 136 is fixed to the inside and proximal side of the first distal side sleeve 134. The first distal side sleeve 134 covers the distal-side outer circumferential surface of the second distal side sleeve 136. A flange 144 which projects diametrically outward and which receives the proximal end of the first distal side sleeve 134 is formed on the outer circumferential surface of the proximal end of the second distal side sleeve 136.

The second distal side sleeve 136 is fixed to the connection sleeve 132 by a screw 142. The rotation member 140 is provided on the outer circumference of the connection sleeve 132 movably along the central axis C of the connection sleeve 132 of the insertion unit 42 and rotatably around the central axis C in response to the rotation of a later-described rotation gear 202 of the rotation force transmission unit 22. The distal end of the rotation member 140 separably contacts on the flange 144 at the proximal end of the second distal side sleeve 136. The outer circumferential surface of the rotation member 140 diametrically outwardly projects as compared with the outer circumferential surface of the flange 144 relative to the central axis C.

The rotation member 140 has a cylindrical member 152 and a diametrically inwardly projecting inward flange 154 at the distal end of the cylindrical member 152. The distal end of the inward flange 154 contacts on the proximal end of the above-mentioned flange 144 of the second distal side sleeve 136. The internal teeth 140a of the rotation member 140 are formed on the inner circumferential surface of the inward flange 154.

An outer circumferential surface (outer circumferential portion) 152a of the cylindrical member 152 is formed into a shape other than a circle; for example, into a polygonal shape such as a substantially equilateral octagonal shape to fit to a later-described fit surface (fit portion) 266 of, for example, the tube proximal portion 88 of the rotation unit 44. Openings 156 which are in communication with the channel 30 are formed in the cylindrical member 152 at appropriate intervals toward the central axis C. The openings 156 are preferably formed on the respective planes of a polygonal shape such as an equilateral octagonal shape of the outer circumferential surface 152a of the cylindrical member 152.

A contact portion 158 is formed in the vicinity of the boundary between the cylindrical member 152 and the inward flange 154 so that a later-described press portion (contact portion) 268 of the rotation unit 44 contacts on the contact portion 158. In this embodiment, the contact portion 158 is inclined diametrically outward and toward the distal side along the central axis C.

An annular distal side spring support portion 160 on which the distal end of a later-described coil spring (urging portion) 180 contacts and supports is formed at the proximal end of the cylindrical member 152. The distal side spring support portion 160 is annularly formed, and is movable on a large-diameter circumferential surface (slide surface) 172 of the outer circumferential surface of the connection sleeve 132 along the axial direction of the central axis C. The distal end of the coil spring 180 is located on the outer circumference of the distal side spring support portion 160.

A substantially cylindrical small-diameter circumferential surface 170 and a substantially cylindrical large-diameter circumferential surface 172 are formed on the outer circumferential surface of the connection sleeve 132. The small-diameter circumferential surface 170 defines the moving direction of the internal teeth 140a of the rotation member 140 along the axial direction of the central axis C. The large-diameter circumferential surface 172 defines the moving direction of the cylindrical member 152 of the rotation member 140 along the axial direction of the central axis C on the proximal side of the small-diameter circumferential surface 170. On the proximal side of the large-diameter circumferential surface 172, a cylindrical surface 174 larger in diameter than the large-diameter circumferential surface 172 is formed. A step 171 is formed between the small-diameter circumferential surface 170 and the large-diameter circumferential surface 172, and a step 173 is formed between the proximal end of the large-diameter circumferential surface 172 and the cylindrical surface 174. A proximal-side moving range of the rotation member 140 can be defined by the steps 171 and 173.

For example, a circular-ring-shaped engagement portion 176 is formed on the proximal side of the cylindrical surface 174. The engagement portion 176 is larger in diameter than the cylindrical surface 174, diametrically outwardly projects, and engages with a later-described engagement portion (protruding portion) 262 of the tube proximal portion 88 of the rotation unit 44. That is, the engagement portion 176 is formed on the outer circumferential surface of the connection sleeve 132 to project diametrically outward relative to the central axis C. The engagement portion 176 has an annular protrusion (protruding portion) 176a, and an annular depression (depressed portion) 176b continuously adjacent to the proximal end of the annular protrusion 176a. The engagement portion 262 of the tube proximal portion 88 of the rotation unit 44 climbs over the annular protrusion 176a and engages with the annular depression 176b.

A proximal-side spring support portion 178 on which the proximal end of the later-described coil spring (urging portion) 180 contacts and bears is formed at the distal end of the annular protrusion 176a, that is, between the cylindrical surface 174 and the annular protrusion 176a. The coil spring 180 is formed on the outer circumferential surface of the connection sleeve 132 and between the proximal-side spring support portion 178 of the connection sleeve 132 and the distal side spring support portion 160 of the rotation member 140. Thus, the coil spring 180 urges the rotation member 140 so that the rotation member 140 contacts on the proximal end of the rotation unit 44 of the second distal side sleeve 136. That is, the coil spring 180 urges the rotation member 140 so that the rotation member 140 separates toward the distal side of the central axis C of the insertion unit 42 along the central axis C.

In the connection sleeve 132, a leaf spring (elastic press member) 182 is fixed to a support portion 193 close to the rear end side of a later-described gear location cavity 192 by a screw 184. The distal end (the distal end to the screw 184) of the leaf spring 182 has a protrusion (insertion apparatus side engagement portion) 182a as an elastic press member which can be fitted into a depressed groove (insertion body side engagement portion) 206a of a later-described collar (support cylinder) 206 of the rotation force transmission unit 22. The protrusion (protruding portion) 182a is formed into a substantially spherical shape, and particularly preferably has inclined surfaces formed on the distal side and proximal side.

When the protrusion 182a of the leaf spring 182 is engaged with the depressed groove 206a, the collar 206 rotates around the longitudinal axis L while sliding on the support portion 193 of the channel 30, so that the rotation force transmission unit 22 is rotatable, but the movement in the axial direction is regulated. As shown in FIG. 8B, the leaf spring 182 is elastically deformable, but the elastic deformation of the leaf spring 182 is regulated by the inner circumferential surface of the cylindrical member 152 of the rotation member 140. That is, the cylindrical member 152 of the rotation member 140 of the insertion unit 42 functions as an assist portion such that its inner circumferential surface in particular can assist the protrusion 182a of the leaf spring 182 in maintaining engagement with the depressed groove 206a of the collar 206. Thus, when the rotation force transmission unit 22 is rotating and the rotation member 140 is rotating accordingly, the movement of the rotation force transmission unit 22 in the axial direction of the longitudinal axis L is prevented.

The proximal side sleeve 138 having a cavity 138a is fixed to the proximal end of the connection sleeve 132. The distal end of the second flexible tube 60 is fixed to the proximal end of the proximal side sleeve 138.

Although not shown, the extensive components 12a are inserted through the space inside the first flexible tube 58, the cavity 134a of the first distal side sleeve 134, the cavity 132a of the connection sleeve 132, the hollow 138a of the proximal side sleeve 138, and the space inside the second flexible tube 60 that are in communication with one another.

The connection sleeve 132, the first distal side sleeve 134, the second distal side sleeve 136, the proximal side sleeve 138, and the rotation member 140 are made of, for example, a metallic material, and are therefore formed to be unbendable relative to the first flexible tube 58 and the second flexible tube 60. For example, even if an external force is applied to the flexible tube connection portion 66 by the inner wall of the large intestine, the flexible tube connection portion 66 does not bend.

Figure 5:
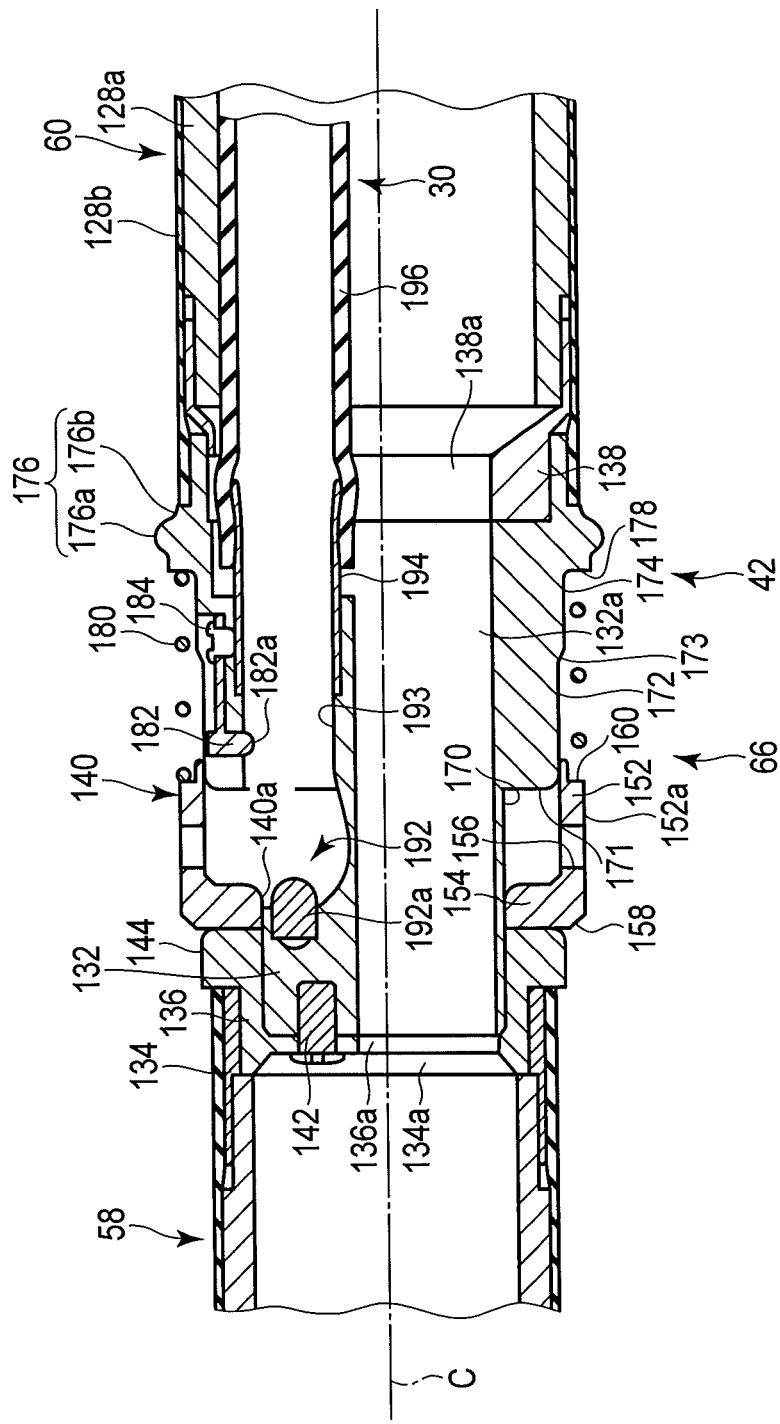
FIG. 5 is a schematic longitudinal sectional view showing a flexible tube connection portion between the first flexible tube and a second flexible tube in the insertion portion of the endoscope of the endoscope system according to the first embodiment.
Figure 6:
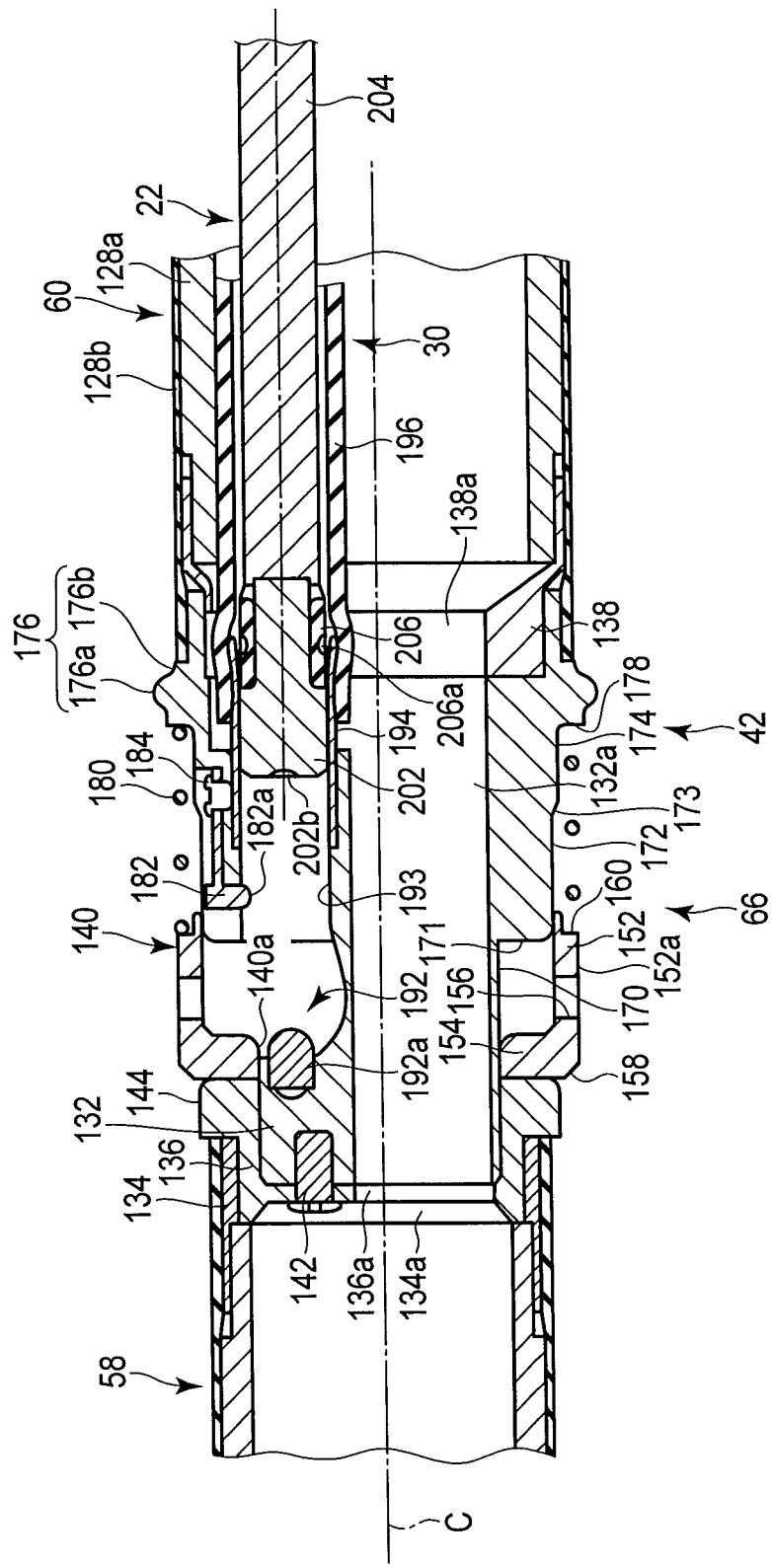
FIG. 6 is a schematic longitudinal sectional view showing how a rotation gear of the rotation force transmission unit (insertion body) is to be disposed in a gear location cavity at the distal end of a channel of an insertion unit of the endoscope of the endoscope system according to the first embodiment or how the rotation force transmission unit is to be removed from the channel.
Figure 7:
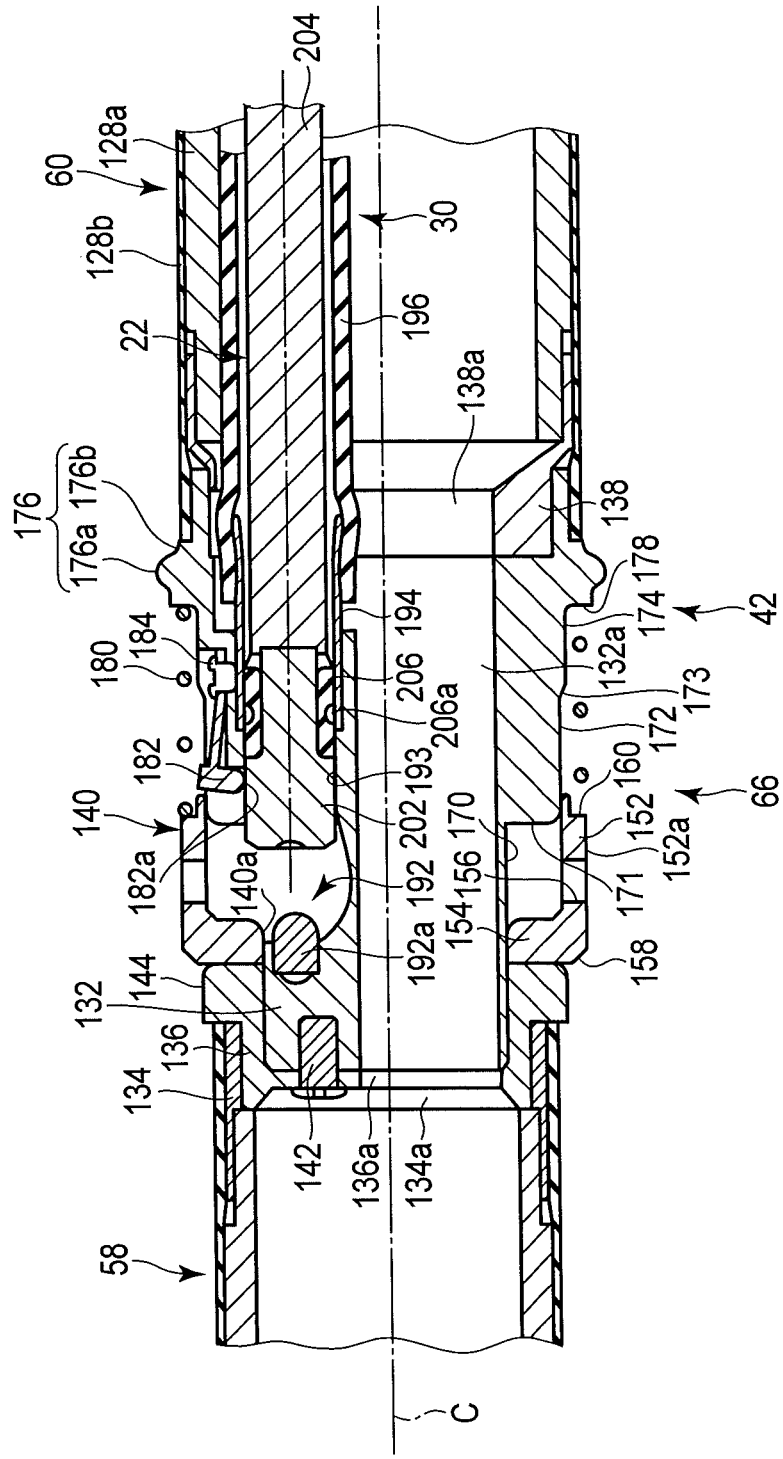
FIG. 7 is a schematic longitudinal sectional view showing how the rotation gear of the rotation force transmission unit (insertion body) is to be disposed in the gear location space at the distal end of the channel of the insertion unit of the endoscope of the endoscope system according to the first embodiment or how the rotation force transmission unit is to be removed from the channel.

As shown in FIG. 5 to FIG. 9, the gear location cavity 192 (opening end portion of the channel 30) in which the later-described rotation gear (rotation force transmission portion) 202 of the rotation force transmission unit 22 is located is formed in the connection sleeve 132. This gear location hollow 192 is open to the outside of the connection sleeve 132. That is, the gear location cavity 192 is in communication with the internal teeth 140a of the rotation member 140. As shown in FIG. 7, the cross section of the gear location cavity 192 at this position is, for example, substantially U-shaped. When the rotation gear 202 is provided in the gear location cavity 192, part (the upper part in FIG. 7) of the rotation gear 202 is located to project from the gear location cavity 192.

A support member 192a which rotatably supports the depression 202b at the distal end of the rotation gear 202 is provided in the gear location cavity 192.

The support portion 193 by which the collar 206 of the rotation force transmission unit 22 is rotatably supported on the proximal side of the gear location cavity 192 is formed in the connection sleeve 132. When the rotation force transmission unit 22 is not provided in the channel 30, the protrusion 182a of the leaf spring 182 projects inward in the diametrical direction of the support portion 193 (toward the longitudinal axis L) as shown in FIG. 5 and FIG. 6. When the collar 206 of the rotation force transmission unit 22 is provided in the support portion 193 and when the depressed groove 206a of the collar 206 is fitted to the protrusion 182a of the leaf spring 182, there is almost no gap between the outer circumferential surface of the collar 206 and the support portion 193, but the movement in the axial direction is regulated, and the rotation around the longitudinal axis L, that is, the sliding around the longitudinal axis L is permitted.

A cylindrical channel sleeve 194 for the rotation force transmission unit 22 is fixed to the connection sleeve 132 at a position which is in communication with the gear location cavity 192. The channel sleeve 194 is watertightly fixed to the connection sleeve 132. The distal end of a channel tube 196 for the rotation force transmission unit 22 is fixed to the outer circumferential surface of the channel sleeve 194. Therefore, the rotation force transmission unit 22 can be inserted through the channel tube 196. The channel tube 196 extends through the insertion unit 42 in the proximal direction along the central axis C.

The channel tube 196 is watertightly fixed to the channel sleeve 146, and is provided to be parallel with a treatment instrument channel tube which is one of the extensive components 12a.

Figure 2A:
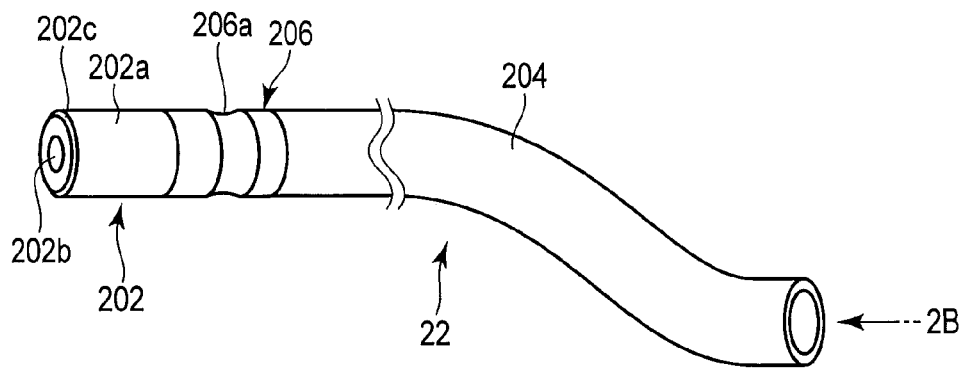
FIG. 2A is a schematic perspective view showing a rotation force transmission unit (insertion body) which is attachable to and detachable from an endoscope of the endoscope system according to the first embodiment.

Here, as shown in FIG. 2A, the rotation force transmission unit 22 has the substantially columnar rotation gear (rotation force transmission portion) 202, a drive shaft 204, and the collar (rotating cylinder) 206 provided on the outer circumference of a connection portion between the rotation gear 202 and the drive shaft 204. The longitudinal axis L of the rotation force transmission unit 22 is defined by the rotation gear 202, the drive shaft 204, and the collar 206.

The rotation gear 202 has an outer circumferential gear portion (external teeth) 202a on its outer circumference. The outer circumferential gear portion 202a is rotatable around the longitudinal axis L in the channel 30, and can mesh with the internal teeth 140a of the rotation member 140. A depression 202b is, for example, substantially conically formed at the distal end of the rotation gear 202, and the depression 202b of the rotation gear 202 is rotatably supported by the support member 192a provided in the gear location cavity 192. Since there is almost no gap between the outer circumferential surface of the collar 206 located on the proximal side of the rotation gear 202 and the support portion 193, the rotation gear 202 rotates while doubly held by the support member 192a and the support portion 193. Therefore, the rotation of the rotation gear 202 can be stabilized.

An inclined surface 202c is preferably formed in the outer circumferential surface at the distal end of the rotation gear 202 so that the protrusion 182a of the leaf spring 182 is easily pushed aside and elastically deformed.

Figure 2B:
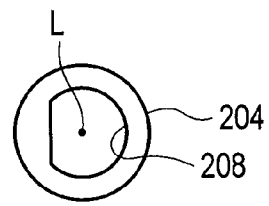
FIG. 2B is a schematic front view from the direction of an arrow 2B in FIG. 2A.

The drive shaft 204 extends toward the proximal side from the proximal end of the rotation gear 202 along the longitudinal axis L, and can rotate the rotation gear 202 if a rotational force around the longitudinal axis L is applied to the proximal end of the drive shaft 204. For example, the drive shaft 204 is formed into multiple layers by stacked metallic wires wound into a cylindrical net form, or formed by a multilayer wire in which right-handed and left-handed wire materials are stacked. The drive shaft 204 has a rotation following capability and flexibility. As shown in FIG. 2B, the proximal end of the drive shaft 204 is, for example, circular. A D-shaped depression 208 into which a later-described D-shaped rotation shaft 214 of the driving source 24 is fitted is formed at the proximal end of the drive shaft 204. Therefore, the rotation of the rotation shaft 214 of the driving source 24 is transmitted to the drive shaft 204, and the rotation of the drive shaft 204 is transmitted to the rotation gear 202.

The collar 206 may be disposed on the outer circumferential surface of the rotation gear 202 as shown in FIG. 6, may be disposed on the outer circumferential surface at the distal end of the drive shaft 204, or may be disposed across the outer circumferential surfaces of the rotation gear 202 and the drive shaft 204. That is, the collar 206 is provided on the outer circumferential surface of at least one of the rotation gear 202 and the drive shaft 204. The collar 206 has the annular depressed groove (insertion body side engagement portion) 206a which can engage with the insertion unit 42. The width of the depressed groove 206a in a direction along the direction of the longitudinal axis L is at such a degree that the protrusion 182a of the leaf spring 182 is provided on the depressed groove 206a. Thus, when the protrusion 182a of the leaf spring 182 engages with the depressed groove 206a of the collar 206, the movement of the collar 206, that is, the rotation force transmission unit 22 along the longitudinal axis L of the channel 30 is prevented. That is, the collar 206 permits the rotation around the longitudinal axis L, and regulates the movement in the axial direction of the longitudinal axis L.

As shown in FIG. 10A, the driving source 24 has a motor main body 212, the rotation shaft 214, and a motor cable 216. The distal end of the motor cable 216 is removably connected to the control unit 14. The outer shape of the cross section of the rotation shaft 214 at right angles with the axial direction of the rotation shaft 214 in the motor main body 212, and the outer shape of the cross section of the motor main body 212 are, for example, D-shaped.

As shown in FIG. 10A, the operation portion 34 is provided with the attachment portion 222 which defines an exit 222a of the proximal end of the drive shaft 204 of the rotation force transmission unit 22 and to which the later-described driving source 24 for transmitting a rotational force to the proximal end of the drive shaft 204 is attached. A holding ring 224 which holds the outer circumference of the motor main body 212 is provided in the attachment portion 222.

The channel tube 196 shown in FIG. 5 to FIG. 8B is in communication with the exit 222a of the attachment portion 222 through the insertion unit 42 and the operation portion 34. Therefore, the proximal end of the channel tube 196 is open at the exit 222a of the attachment portion 222.

In this way, the gear location cavity 192, the support portion 193, the channel sleeve 194, the channel tube 196, and the attachment portion 222 are defined from the distal end to the proximal end in order in the flexible tube connection portion 66 and the second flexible tube 60 of the insertion unit 42, so that the channel 30 as an insertion path through which the rotation force transmission unit 22 is inserted is formed.

Figure 8A:
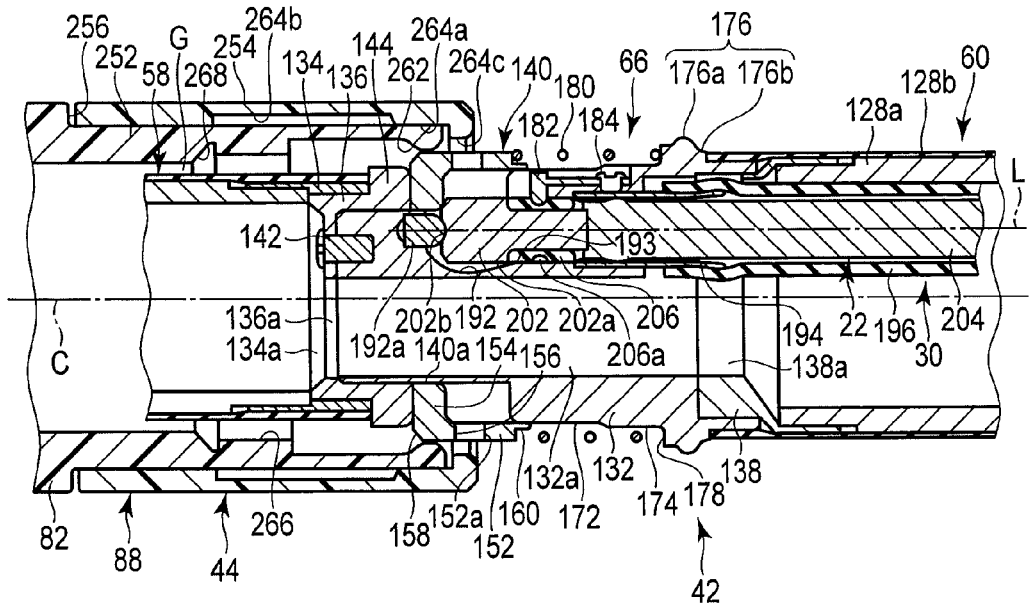
FIG. 8A is a schematic longitudinal sectional view showing how a rotation unit of the insertion portion of the endoscope of the endoscope system according to the first embodiment is moved to the proximal side of the central axis of the insertion unit to attach the rotation unit to the outer circumference of the insertion unit, or showing a state immediately after the rotation unit is removed from the outer circumference of the insertion unit.
Figure 8B:
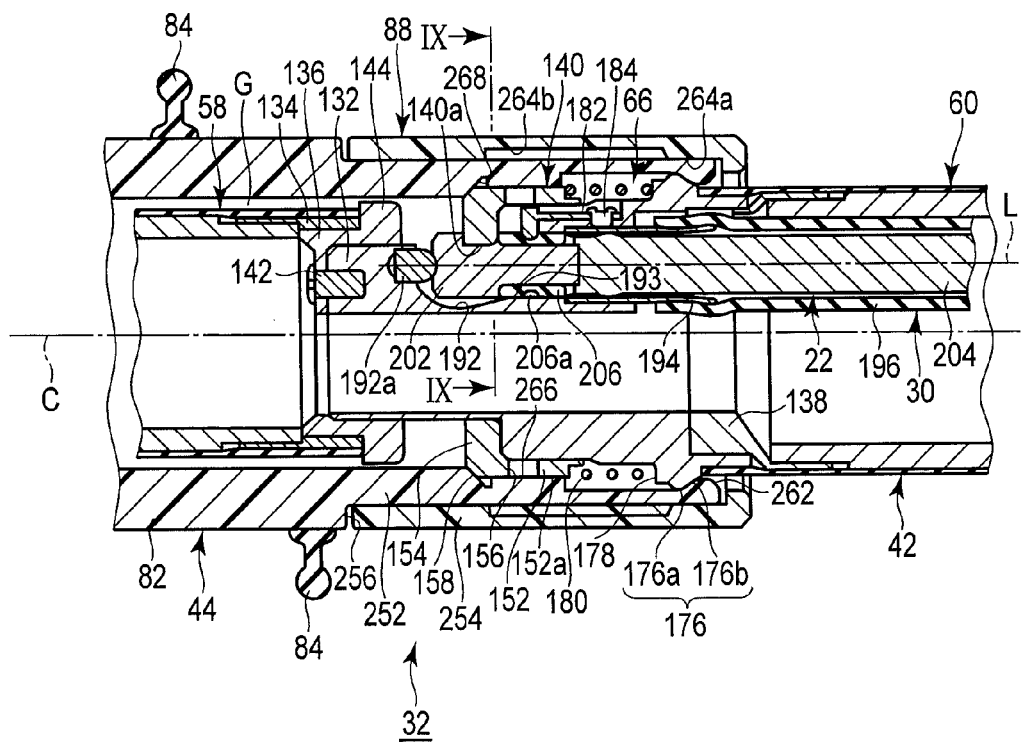
FIG. 8B is a schematic longitudinal sectional view showing how the rotation unit of the insertion portion of the endoscope of the endoscope system according to the first embodiment is attached to the outer circumference of the insertion unit.

As shown in FIG. 8A and FIG. 8B, the rotation unit 44 is movable along the axial direction of the central axis C of the insertion unit 42. In particular, the rotation unit 44 is attachable to and detachable from the insertion unit 42 through the distal hard portion 52.

The tube body 82 of the rotation unit 44 is made of a resin material such as polyurethane. The tube body 82 has a gap G between the tube body 82 and the outer circumferential surface of the bending portion outer tube 108 shown in FIG. 4 as well as the outer circumferential surface of the first flexible tube 58 shown in FIG. 8B. That is, the tube body 82 is provided to have the gap G between the tube body 82 and the outer circumferential portion of the insertion unit 42. This prevents friction from being caused between the insertion unit 42 and the tube body 82 when the rotation unit 44 rotates relative to the insertion unit 42.

The tube distal portion 86 is made of a material such as a rubber material softer than the tube body 82. As shown in FIG. 4, the inner circumferential portion of the tube distal portion 86 is formed so that the gap G between the rotation unit 44 and the bending portion outer tube 108 is smaller than in the part located on the inner circumferential side of the tube body 82.

Figure 9:
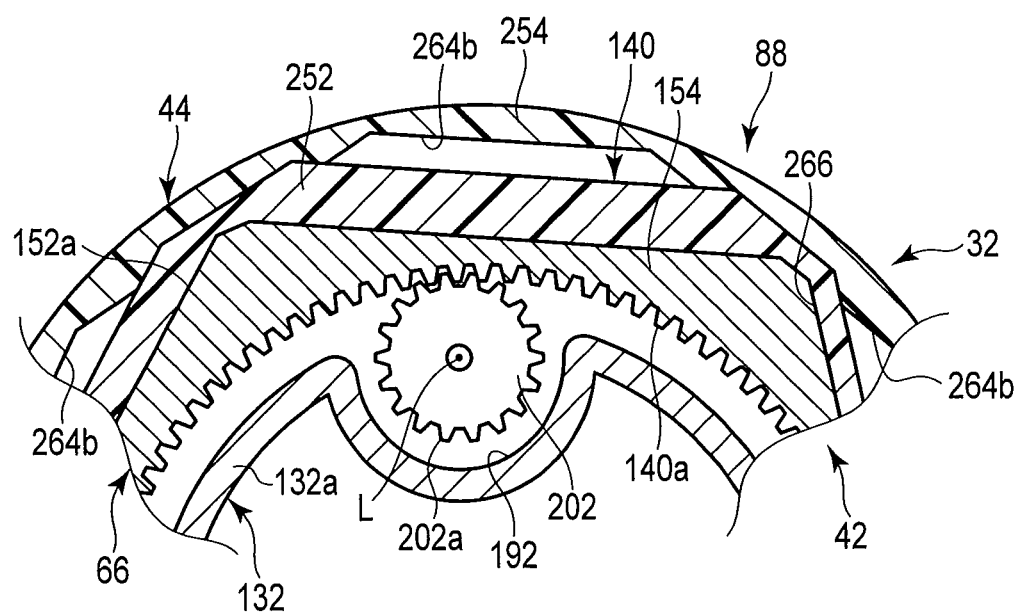
FIG. 9 is a schematic cross sectional view of a position taken along the line IX-IX in FIG. 8B.

According to this embodiment, the tube proximal portion (cylindrical portion) 88 of the rotation unit 44 has an inner cylindrical portion 252 integrated with the tube body 82, and an outer cylindrical portion 254 which is more rigid than the inner cylindrical portion 252 and which is a separate member. The outer cylindrical portion 254 is provided on the outer circumference of the inner cylindrical portion 252 movably along the axial direction of the central axis C. As shown in FIG. 9, the inner circumferential surface of the outer cylindrical portion 254 is fitted to the outer circumferential surface of the inner cylindrical portion 252, and cannot rotate around the central axis C.

The tube proximal portion 88 has a contact portion 256 which regulates the movement of the outer cylindrical portion 254 toward the distal side along the axial direction of the central axis C.

The inner cylindrical portion 252 has the engagement portion 262 which is attachable to and detachable from the outer circumferential surface of the connection sleeve 132. More specifically, the inner cylindrical portion 252 has, on its proximal-side inner circumferential surface, the protruding engagement portion 262 which can engage with the annular depression 176b of the engagement portion 176 of the flexible tube connection portion 66. The inside diameter of the engagement portion 262 is smaller than the maximum outside diameter of the annular protrusion 176a of the engagement portion 176 of the flexible tube connection portion 66, and is formed to be substantially equal to the minimum outside diameter of the annular depression 176b of the engagement portion 176 of the flexible tube connection portion 66. Thus, when the rotation unit 44 moves from a position shown in FIG. 8A to a position shown in FIG. 8B, the diametrically inwardly projecting engagement portion 262 of the tube proximal portion 88 of the rotation unit 44 is elastically deformed together with its peripheral part, and then climbs over the annular protrusion 176a of the engagement portion 176 of the flexible tube connection portion 66 and engages with the annular depression 176b. The outer cylindrical portion 254 has, on its inner circumferential side, a regulation portion 264a which regulates the diametrically outward expansion of the engagement portion 262 resulting from the elastic deformation, and depressions 264b (see FIG. 9) formed on the distal side of the regulation portion 264a. Thus, when the engagement portion 262 is located inside the depression 264b, outward elastic deformation of the engagement portion 262 is permitted. When the engagement portion 262 is located out of the depression 264b, outward elastic deformation of the engagement portion 262 is regulated. Thus, the tube proximal portion 88 can apply sufficient force to maintain the engagement of the engagement portions 176 and 262.

According to this embodiment, there is more than one depression 264b formed in the inner circumference of the outer cylindrical portion 254, and the depressions 264b are not formed annularly all around the inner circumference of the outer cylindrical portion 254. Thus, even if the outer cylindrical portion 254 has moved to the proximal side relative to the inner cylindrical portion 252 during the use of the endoscope 12, the elastic deformation of the engagement portion 262 is regulated by the ends of the depressions 264b.

A diametrically inwardly projecting flange 264c is preferably formed at the proximal end of the outer cylindrical portion 254. The inside diameter of this flange 264c is larger than the inside diameter of the engagement portion 262 at the proximal end of the inner cylindrical portion 252.

The fit surface 266 which has the same shape as the outer circumferential surface 152a of the cylindrical member 152 of the rotation member 140 and which is fitted to the outer circumferential surface 152a of the cylindrical member 152 of the rotation member 140 is formed on the inner circumference of the inner cylindrical portion 252 of the tube proximal portion 88 closer to the distal side than the engagement portion 262. The outer circumferential surface 152a of the cylindrical member 152 of the rotation member 140 and the fit surface 266 of the inner cylindrical portion 252 shown in FIG. 9 are formed into, for example, a substantially octagonal shape.

As shown in FIG. 8A and FIG. 8B, the press portion 268 which projects diametrically inward toward the central axis C as compared with the fit surface 266 is formed on the side of the tube proximal portion 88 closer to the distal side than the fit surface 266. The press portion 268 is provided to be able to contact on the contact portion 158 of the rotation member 140 away from the engagement portion 262. The minimum inside diameter of the press portion 268 is larger than the outside diameter of the first flexible tube 58, and the gap G is provided between the inner circumferential surface of the inner cylindrical portion 252 and the outer circumferential surface of the first flexible tube 58.

The fin portion 84 extending on the outer circumferential portion of the tube body 82 is made of, for example, a rubber material. The fin portion 84 is fixed to the tube body 82 by, for example, adhesive bonding or welding. As shown in FIG. 1, the fin portion 84 spirally extends clockwise when viewed from the proximal direction. When the insertion portion 32 of the endoscope 12 is inserted in the lumen in the small intestine or the large intestine, the fin portion 84 of the rotation unit 44 contacts on the wall of the lumen. In this condition, the rotation member 140 and the rotation unit 44 are rotated relative to the insertion unit 42 around the central axis C. As a result, propulsion in a direction along the axial direction of the central axis C is applied to the insertion portion 32.

Now, the operation of the endoscope system 10 according to this embodiment is described. Here, an assembly procedure for attaching the rotation force transmission unit 22 and the rotation unit 44 to the insertion unit 42 and attaching the driving source 24 to the operation portion 34 is mainly described.

The rotation gear 202 of the rotation force transmission unit 22 shown in FIG. 2A is introduced, from its distal end, into the gear location cavity 192 of the flexible tube connection portion 66 through the attachment portion 222, the channel tube 196, the channel sleeve 194, and the support portion 193.

The rotation gear 202 of the rotation force transmission unit 22 is moved from a position shown in FIG. 6 to a position shown in FIG. 7. At the same time, the protrusion 182a of the leaf spring 182 is pushed aside by the inclined surface 202c of the rotation gear 202 to elastically deform the leaf spring 182 and then evacuate the leaf spring 182 to the upper side in FIG. 7. The protrusion 182a of the leaf spring 182 moves along the outer circumferential surface of the external teeth 202a of the rotation gear 202. The protrusion 182a of the leaf spring 182 is engaged with the depressed groove 206a of the collar 206 by its elastic force. At the same time, the depression 202b of the rotation gear 202 is supported by the support member 192a. The longitudinal axis L of the rotation force transmission unit 22 is parallel with the central axis C of the insertion unit 42.

In this case, since the rotation member 140 is not provided outside the leaf spring 182, the leaf spring 182 can evacuate to the upper side in FIG. 7. Therefore, if the whole rotation force transmission unit 22 is pulled toward the rear end of the channel 30, the leaf spring 182 is disengaged from the depressed groove 206a of the collar 206 of the rotation force transmission unit 22.

When the rotation force transmission unit 22 is disposed at a predetermined position in the channel 30 as shown in FIG. 8A, the proximal end of the drive shaft 204 is located in the attachment portion 222 or in the vicinity of the attachment portion 222 as shown in FIG. 10A. In this condition, the driving source 24 shown in FIG. 10A is attached to the D-shaped attachment portion 222 shown in FIG. 10B, and the rotation shaft 214 is fitted into the D-shaped depression 208 at the proximal end of the drive shaft 204.

The rotation unit 44 is then moved toward the proximal end of the insertion unit 42 while being rotated around the central axis C. That is, the engagement portion 262 at the proximal end of the tube proximal portion 88 of the rotation unit 44 is moved toward the proximal side through the outside of the rotation member 140 of the flexible tube connection portion 66. The rotation unit 44 is appropriately rotated in the circumferential direction to bring into the same direction the outer circumferential surface 152a of the cylindrical member 152 of the rotation member 140 and the fit surface 266 of the inner cylindrical portion 252 of the rotation unit 44 so that they can fit with each other. The fit surface 266 of the inner cylindrical portion 252 is then fitted to the outer circumferential surface 152a of the cylindrical member 152 of the rotation member 140.

In this condition, the rotation unit 44 located at a position shown in FIG. 8A is relatively moved to the proximal side of the insertion unit 42 up to a position shown in FIG. 8B along the axial direction of the central axis C of the connection sleeve 132. Thus, the contact portion 158 of the rotation member 140 is pressed toward the proximal side by the press portion 268 of the rotation unit 44. The rotation member 140 is moved to the proximal side in the axial direction of the central axis C of the connection sleeve 132 along the large-diameter circumferential surface 172 against the urging force of the coil spring 180. That is, the press portion (contact portion) 268 can move the rotation member 140 to the proximal side of the insertion unit 42 against the urging force of the coil spring 180.

If the regulation portion 264a of the outer cylindrical portion 254 is located away from the position of the engagement portion 262 of the inner cylindrical portion 252, the outer cylindrical portion 254 is then moved to the proximal side to locate the depressions 264b outside the engagement portion 262 of the inner cylindrical portion 252.

As shown in FIG. 8B, the internal teeth 140a of the rotation member 140 and the external teeth 202a of the rotation gear 202 mesh with each other, and the engagement portion 262 of the inner cylindrical portion 252 climbs over the annular protrusion 176a of the engagement portion 176 of the flexible tube connection portion 66 of the insertion unit 42 and engages with the annular depression 176b adjacent on the proximal side. That is, the press portion (contact portion) 268 disposes the rotation member 140 on the outer circumference of the rotation gear 202 while the engagement portion 262 is engaged with the outer circumferential surface of the connection sleeve 132. At the same time, the engagement portion 262 of the rotation unit 44 can engage with the engagement portion 176 on the outer circumferential surface of the connection sleeve 132 against the urging force of the coil spring 180. The outer cylindrical portion 254 is then moved relative to the inner cylindrical portion 252 along the axial direction of the central axis C, so that the elastic deformation that diametrically outwardly expands the engagement portion 262 is regulated.

Thus, the rotation unit 44 is engaged with and fixed to the insertion unit 42.

In this case, since the cylindrical member 152 of the rotation member 140 is located on the outer circumference of the leaf spring 182, the inner circumferential surface of the cylindrical member 152 regulates the elastic deformation of the protrusion 182a of the leaf spring 182 to the upper side in FIG. 8B.

The insertion portion 32 of the endoscope 12 is available in this state. That is, the rotation unit 44 of the insertion portion 32 is rotatable relative to the central axis C in the first direction and the second direction.

For example, when the rotation unit 44 of the insertion portion 32 is rotated in the first direction, the position indicated by the sign 78a in the rotational operation input switch 78 shown in FIG. 1 and FIG. 3 is pressed while the endoscope system 10 shown in FIG. 1 is active. A signal of the pressing of the rotational operation input switch 78 is input to the control unit 14 via the universal cable 36 and the connector 36a. The control unit 14 rotates the rotation shaft 214 of the driving source 24 in the first direction via the motor cable 216 and the motor main body 212. In response to the rotation of the rotation shaft 214 in the first direction, the drive shaft 204 rotates in the first direction around the longitudinal axis L. As a result of the rotation of the drive shaft 204 in the first direction, the rotation force is transmitted to the rotation gear 202 via the collar 206, and the rotation gear 202 rotates in the first direction around the longitudinal axis L. Therefore, the rotation member 140 in mesh with the rotation gear 202 rotates in the first direction around the central axis C. Together with the rotation of the rotation member 140 in the first direction around the central axis C, the rotation unit 44 fitted to the rotation member 140 rotates in the first direction around the central axis C.

When the rotation unit 44 of the insertion portion 32 is rotated in the second direction, the position indicated by the sign 78b in the rotational operation input switch 78 is pressed while the endoscope system 10 shown in FIG. 1 is active.

According to the present embodiment, the fin portion 84 spirally extends clockwise when viewed from the proximal direction. Therefore, if the rotation member 140 and the rotation unit 44 rotate clockwise (in the first direction) when viewed from the proximal direction, propulsion in the distal direction is applied to the insertion portion 32. Thus, the insertability of the insertion portion 32 in the lumen is improved. On the other hand, if the rotation member 140 and the rotation unit 44 rotate counterclockwise (in the second direction) when viewed from the proximal direction, propulsion in the proximal direction is applied to the insertion portion 32. Thus, the removability of the insertion portion 32 in the lumen is improved.

After the use of the endoscope 12, the endoscope 12 is washed, disinfected, and sterilized, and then reused. This procedure is briefly described.

The outer cylindrical portion 254 of the rotation unit 44 is moved to the proximal side relative to the inner cylindrical portion 252 to locate the depressions 264b of the outer cylindrical portion 254 outside the engagement portion 262. In this condition, the engagement portion 262 of the inner cylindrical portion 252 of the rotation unit 44 located in the annular depression 176b of the engagement portion 176 of the flexible tube connection portion 66 of the insertion unit 42 is elastically deformed to climb over the annular protrusion 176a so that the engagement portion 262 of the rotation unit 44 is moved closer to the distal side of the insertion unit 42 than the engagement portion 176 of the insertion unit 42. The engagement portion 262 at the proximal end of the tube proximal portion 88 of the rotation unit 44 is then moved toward the distal side through the outside of the rotation member 140 of the flexible tube connection portion 66.

At the same time, the urging force of coil spring 180 assists the disengagement of the engagement portions 176 and 262, and moves the rotation member 140 to the distal side of the insertion unit 42 into contact with the proximal end of the flange 144. That is, the fitting of the outer circumferential surface 152a of the cylindrical member 152 of the rotation member 140 and the fit surface 266 of the inner cylindrical portion 252 of the rotation unit 44 is released, and the outer circumferential gear portion of the rotation gear 202 is brought out of mesh with the internal teeth 140a of the rotation member 140. At the same time, the rotation member 140 is kept in position at the distal side (front side) from the outer circumference of the leaf spring 182 by the coil spring 180, so that the leaf spring 182 is elastically deformable.

The driving source 24 and the rotation force transmission unit 22 are then strongly pulled to the near side from the proximal end of the channel 30. Thus, the leaf spring 182 is elastically deformed against the spring urging force of the leaf spring 182, and the protrusion 182a of the leaf spring 182 which has engaged with the depressed groove 206a of the collar 206 is disengaged. Accordingly, the rotation force transmission unit 22 can be removed from the channel 30.

The protrusion 182a of the leaf spring 182 moves relative to the outer circumferential surface of the collar 206, the external teeth 202a of the rotation gear 202, and the inclined surface 202c in order into the state shown in FIG. 6. The rotation force transmission unit 22 is then completely removed from the channel 30 as shown in FIG. 5.

That is, the rotation force transmission unit 22 can be easily attached to and detached from the channel 30.

In this case, the openings 156 of the rotation member 140 are kept at the position facing the gear location cavity 192 by the coil spring 180. The insertion path can be therefore ensured when, for example, a washing fluid or a brush is inserted into the channel 30 through the attachment portion 222, the channel tube 196, the channel sleeve 194, and the gear location cavity 192. Thus, the inside of the channel 30 can be washed by the use of the unshown brush or the like while the rotation unit 44 and the rotation force transmission unit 22 are removed from the insertion portion 32. Therefore, the insertion unit 42 and the operation portion 34 can be easily washed, disinfected, and sterilized.

That is, when the rotation unit 44 is removed from the insertion unit 42, the coil spring 180 assists the removal, and functions to keep the rotation member at the predetermined position so that the channel 30 can be easily washed.

As described above, the following can be said according to this embodiment.

When the rotation unit 44 is attached to the insertion unit 42, no additional components for the attachment are needed. That is, when the rotation unit 44 is attached to the insertion unit 42, the fit surface 266 of the rotation unit 44 is aligned with the direction in which the fit surface 266 can be fitted to the outer circumferential surface 152a of the rotation member 140. The contact portion 158 of the rotation member 140 is then pressed toward the proximal side of the insertion unit 42 by the press portion 268 against the urging force of the coil spring 180, and the engagement portion 262 of the rotation unit 44 is then engaged with the engagement portion 176 of the connection sleeve 132. As a result, the attachment is completed. Thus, the rotation unit 44 can be easily attached to the insertion unit 42.

When the rotation unit 44 is detached from the insertion unit 42, no additional components for the detachment are needed. That is, when the rotation unit 44 is detached from the insertion unit 42, the engagement portion 262 of the rotation unit 44 is moved to the distal side of the insertion unit 42, and is then disengaged from the engagement portion 176 of the connection sleeve 132. Thus, the spring urging force of the coil spring 180 is used so that the press portion 268 of the rotation unit 44 is moved to the distal side of the insertion unit 42 by the contact portion 158 of the rotation member 140. That is, the coil spring 180 assists the detachment of the rotation unit 44 from the insertion unit 42. Although the movement of the rotation member 140 is regulated by the flange 144 of the second distal side sleeve 136, the detachment of the rotation unit 44 from the insertion unit 42 is completed by moving the rotation unit 44 to the distal side of the insertion unit 42. Thus, the rotation unit 44 can be easily detached from the insertion unit 42.

When the rotation unit 44 is thus attached to or detached from the insertion unit 42, the deformability of the engagement portion 262 of the rotation unit 44 can be controlled by moving the outer cylindrical portion 254 in the axial direction of the central axis C relative to the inner cylindrical portion 252 of the tube proximal portion 88 of the rotation unit 44. That is, during the use of the endoscope 12, the outer circumferential surface of the engagement portion 262 is held without any gap so that the engagement portion 262 of the rotation unit 44 is difficult deform. When the rotation unit 44 is attached to or detached from the insertion unit 42, a gap (the depressions 264b) can be provided to hold the engagement portion 262 of the rotation unit 44 so that the engagement portion 262 of the rotation unit 44 is easy to deform.

According to this embodiment, the depressions 264b formed in the inner circumference of the outer cylindrical portion 254 are circumferentially divided, and are not formed annularly all around the inner circumference of the outer cylindrical portion 254. Thus, even if the outer cylindrical portion 254 has moved to the proximal side relative to the inner cylindrical portion 252 during the use of the endoscope 12, the circumferential ends of the depressions 264b are partly fitted to the outer circumferential surface of the inner cylindrical portion 252 without any gap, and the elastic deformation of the engagement portion 262 is regulated. This prevents the rotation unit 44 from falling off the insertion unit 42 during the use of the endoscope 12.

Consequently, in the endoscope 12 according to this embodiment, the rotation unit 44 can be easily attached to the insertion unit 42, and assembling efficiency can be improved.

According to this embodiment, the coil spring 180 is used to energize the rotation member 140 to the distal side, so that, for example, when the channel 30 of the insertion unit 42 is washed, the openings 156 of the rotation member 140 face the gear location hollow 192 of the channel 30. Thus, a washing fluid or a brush can be passed through the openings 156 of the rotation member 140 on the distal side, for example, from the proximal side of the channel 30, and the washing performance in the channel 30 can be enhanced. The outer circumferential surface of the insertion unit 42 can also be easily washed.

In the meantime, a flexible tube through which a torque tube can be inserted can be attached to or detached from a spiral propulsion portion according to, for example, Jpn. Pat. Appln. KOKAI Publication No. 2005-288035. When the torque tube is fixed by the spiral propulsion portion, the distal end of the flexible tube is pressed inward from the outside. The distal end of the torque tube inserted through the flexible tube is coupled to a gear mechanism of the spiral propulsion portion.

In the structure according to Jpn. Pat. Appln. KOKAI Publication No. 2005-288035, the flexible tube is attachable and detachable, but the torque tube inserted through the flexible tube is coupled to the gear mechanism. Therefore, it takes time to attach or detach the torque tube to or from the spiral propulsion portion. Thus, when, for example, the flexible tube and the torque tube are disposable, it is troublesome to detach the torque tube from the gear mechanism or attach the torque tube to the gear mechanism.

According to this embodiment, it is possible to provide an insertion body which can be easily attached to or detached from a predetermined position of an insertion apparatus and which is ready for use when inserted at the predetermined position of the insertion apparatus, an insertion apparatus in which this insertion body is provided, and an insertion system having the insertion body and the insertion apparatus.

The rotation force transmission unit (insertion body) 22 is attachable to and detachable from the channel 30 of the endoscope 12 having the elongated insertion unit 42, the cylindrical rotation unit 44, and the channel 30, and can transmit a rotational force to the cylindrical rotation unit 44 via the rotation member 140 while being provided in the channel 30.

When the rotation force transmission unit 22 is attached to the channel 30 of the insertion unit 42, it is possible to permit the rotation of the rotation force transmission unit 22 around the longitudinal axis L and regulate the movement in the direction of the longitudinal axis L only by engaging the protrusion 182a of the leaf spring 182 with the depressed groove 206a of the collar 206. Thus, the rotation force transmission unit 22 can be easily attached to the channel 30.

On the other hand, when the rotation force transmission unit 22 is detached from the channel 30 of the insertion unit 42, it is only necessary to strongly pull the rotation force transmission unit 22 to the proximal side relative to the channel 30 and then disengage the protrusion 182a of the leaf spring 182 from the depressed groove 206a of the collar 206. Therefore, the rotation force transmission unit 22 can be easily detached from the channel 30.

To only obtain such advantageous effects, the engagement portion 262 and the press portion (contact portion) 268 do not necessarily need to be provided in the rotation unit 44.

When the rotation force transmission unit 22 and the rotation unit 44 are attached to the insertion unit 42, the elastic deformation of the leaf spring 182 can be inhibited by the inner circumferential surface of the cylindrical member 152 of the rotation member 140. Thus, it is possible to prevent the rotation force transmission unit 22 from moving in the direction of its longitudinal axis L relative to the channel 30 during the use of the endoscope 12. That is, the external teeth 202a of the rotation gear 202 and the internal teeth 140a of the rotation member 140 can be kept in mesh with each other during the use of the endoscope 12.

Therefore, it is possible to easily attach or detach the rotation force transmission unit 22 to or from the channel 30 without the trouble or costs required for components such as other tools. That is, regarding the endoscope 12 according to this embodiment, the rotation force transmission unit 22 can be easily attached to the insertion unit 42, and assembling efficiency can be improved.

The rotation force transmission unit 22 according to this embodiment is supported by what is known as both-ends-supporting to rotate so that the depression 202b at the distal end of the rotation gear 202 is supported by the support member 192a and so that the collar 206 at the proximal end of the rotation gear 202 is supported on the support portion 193 by the leaf spring 182. Thus, it is possible to effectively prevent the rotation gear 202 from being out of alignment with the longitudinal axis L while being rotated or from moving to the proximal side along the longitudinal axis L.

Although a motor is used as the driving source 24 in the example described according to this embodiment, the rotation shaft 214 may be manually rotated.

Now, the second embodiment is described with reference to FIG. 11A and FIG. 11B. This embodiment is a modification of the first embodiment. The same components as the components described in the first embodiment are indicated by the same reference signs and are not described in detail.

In the example described according to this embodiment, the rotation force transmission unit 22 is incorporated in the channel 30 of the insertion unit 42.

The flexible tube connection portion 66 according to this embodiment has a connection sleeve 302 made of, for example, a metallic material or a hard resin material to be a base, a distal side sleeve 304, and a ring-shaped rotation member 306. The connection sleeve 302 has a central axis C which is defined by the insertion unit 42.

The distal side sleeve 304 has a cavity 304a through which the extensive components 12a (see FIG. 4) that are not shown here are inserted. Similarly, the connection sleeve 302 has a hollow 302a through which the extensive components 12a (see FIG. 4) that are not shown here are inserted and which is in communication with the hollow 304a of the distal side sleeve 304.

The distal side sleeve 304 is provided at the proximal end of the first flexible tube 58. The distal end of the connection sleeve 302 is fixed to the inside of the proximal end of the distal side sleeve 304.

The rotation member 306 is provided on the outer circumference of the connection sleeve 302 movably along the central axis C of the connection sleeve 302 of the insertion unit 42 and rotatably around the central axis C. The distal end of the rotation member 306 separably abuts on the proximal end of the distal side sleeve 304.

The rotation member 306 has an inner cylindrical member 312 having internal teeth (inner circumferential gear portion) 312a on the inner circumferential surface, and an outer cylindrical member 314 which covers the distal side and outer circumference of the inner cylindrical member 312. While the inner cylindrical member 312 is preferably made of a metallic material, either a metallic material a resin material may be used for the outer cylindrical member 314. The distal end of the outer cylindrical member 314 contacts on the proximal end of the above-mentioned distal side sleeve 304.

An outer circumferential surface (outer circumferential portion) 314a of the outer cylindrical member 314 is formed into a shape other than a circle, for example, a substantially equilateral octagonal shape to fit to a later-described fit surface (fit portion) 352 of, for example, the tube proximal portion 88 of the rotation unit 44. Openings 316 which are in communication with the channel 30 are formed through the inner cylindrical member 312 and the outer cylindrical member 314 at appropriate intervals toward the central axis C. The openings 316 are preferably formed on the respective planes of, for example, an equilateral octagonal shape of the outer circumferential surface 314a of the outer cylindrical member 314.

A contact portion 314b on which a later-described press portion (contact portion) 354 of the rotation unit 44 contacts is formed on the distal-side outer circumferential surface of the outer cylindrical member 314. In this embodiment, the contact portion 314b is inclined diametrically outward and toward the distal side along the central axis C.

A substantially cylindrical slide surface 322 which defines the movement direction of the inner circumferential surface of the outer cylindrical member 314 of the rotation member 306 along the axial direction of the central axis C is formed on the outer circumferential surface of the connection sleeve 302.

For example, a circular-ring-shaped engagement portion (protruding portion) 324 is formed on the proximal side of the slide surface 322. The engagement portion 324 is larger in diameter than the slide surface 322, diametrically outwardly projects, and engages with a later-described engagement portion (protruding portion) 356 of the tube proximal portion 88 of the rotation unit 44. That is, the engagement portion 324 is formed on the outer circumferential surface of the connection sleeve 302 to project diametrically outward relative to the central axis C.

The distal side of the engagement portion 324 on the outer circumferential surface of the connection sleeve 302 is formed on the distal side close to the central axis C, and the side located apart from the central axis C is formed on an inclined surface 324a located closer to the proximal side. The proximal side of the engagement portion 324 on the outer circumferential surface of the connection sleeve 302 is formed as, for example, an orthogonal plane 324b which intersects at right angles with the central axis C. The engagement portion 356 of the tube proximal portion 88 of the rotation unit 44 is structured to easily climb over the inclined surface 324a of the engagement portion 324 on the outer circumferential surface of the connection sleeve 302 and move to the proximal side but to be difficult to move to the distal side if engaged with the orthogonal plane 324b.

The distal end of the second flexible tube 60 is fixed to the proximal end of the connection sleeve 302.

Although not shown, the extensive components 12a are inserted through the space inside the first flexible tube 58, the cavity 304a of the distal side sleeve 304, the cavity 302a of the connection sleeve 302, and the space inside the second flexible tube 60 that are in communication with one another.

The connection sleeve 302, the distal side sleeve 304, the rotation member 306 are made of, for example, a metallic material, and are therefore formed to be unbendable relative to the first flexible tube 58 and the second flexible tube 60. For example, even if an external force is applied to the flexible tube connection portion 66 by the inner wall of the large intestine, the flexible tube connection portion 66 does not bend.

A gear location cavity (opening end portion of the channel 30) 332 in which a later-described rotation gear (rotation force transmission portion) 342 of the rotation force transmission unit 22 is located is formed in the connection sleeve 302. This gear location cavity 332 is open to the outside of the connection sleeve 302. The cross section of the gear location hollow 332 at this position is, for example, substantially U-shaped. When the rotation gear 342 is provided in the gear location cavity 332, part of the rotation gear 342 is located to project from the gear location space 332.

A depressed support portion 332a which rotatably supports the distal end of the rotation gear 342 is formed in the gear location cavity 332.

The connection sleeve 302 has an annular portion 334 in which an O-ring 336 is provided on the proximal side of the gear location cavity 332. The O-ring 336 prevents a liquid from coming into the part of the channel 30 closer to the proximal side than the O-ring 336.

The cylindrical channel sleeve 194 for the rotation force transmission unit 22 is fixed to the connection sleeve 302 at a position which is in communication with the gear location cavity 332. The channel sleeve 194 is watertightly fixed to the connection sleeve 302. The distal end of the channel tube 196 for the rotation force transmission unit 22 is fixed to the outer circumferential surface of the channel sleeve 194. Therefore, the rotation force transmission unit 22 can be inserted through the channel tube 196. The channel tube 196 extends through the insertion unit 42 in the proximal direction along the central axis C.

Here, the rotation force transmission unit 22 has a substantially columnar rotation gear (rotation force transmission portion) 342, and the drive shaft 204. The longitudinal axis L of the rotation force transmission unit 22 is defined by the rotation gear 342 and the drive shaft 204.

The rotation gear 342 has, on its outer circumference, an outer circumferential gear portion (external teeth) 342a, a projecting portion 342b which is provided on the distal side of the outer circumferential gear portion 342a and which is supported by the support portion 332a of the connection sleeve 302, and an annular receiving portion 342c which is provided on the proximal side of the outer circumferential gear portion (external teeth) 342a and in which the O-ring 336 is provided.

In this way, the gear location space 332, the annular portion 334, the channel sleeve 194, the channel tube 196, and the attachment portion 222 are defined from the distal end to the proximal end in order in the flexible tube connection portion 66 and the second flexible tube 60 of the insertion unit 42, so that the channel 30 as an insertion path through which the rotation force transmission unit 22 is inserted is formed.

The rotation unit 44 is movable along the axial direction of the central axis C of the insertion unit 42. In particular, the rotation unit 44 is attachable to and detachable from the insertion unit 42 through the distal hard portion 52.

According to this embodiment, the tube proximal portion 88 of the rotation unit 44 is integrated with the tube body 82. The tube proximal portion 88 has the fit surface 352 which is fitted to the outer circumferential surface 314a of the rotation member 306, the press portion 354 which is provided on the distal side of the fit surface 352 and which regulates the movement of the rotation member 306 to the distal side along the axial direction of the central axis C, and the engagement portion 356 which is provided on the proximal side of the fit surface 352 and which can engage with the engagement portion 324 of the connection sleeve 302. The press portion 354 is provided to be able to contact on the contact portion 314b of the rotation member 306 away from the engagement portion 356. The engagement portion 356 has, on the proximal side, an inclined surface 356a which preferably has the same inclination as the inclined surface 324a of the engagement portion 324 of the connection sleeve 302, and has, on the distal side, an orthogonal plane 356b which intersects at right angles with the central axis C in the same manner as the orthogonal plane 324b of the engagement portion 324 of the connection sleeve 302. The inside diameter of the engagement portion 356 is formed to be larger than the outer circumferential surface of the rotation member 306.

Figure 11A:
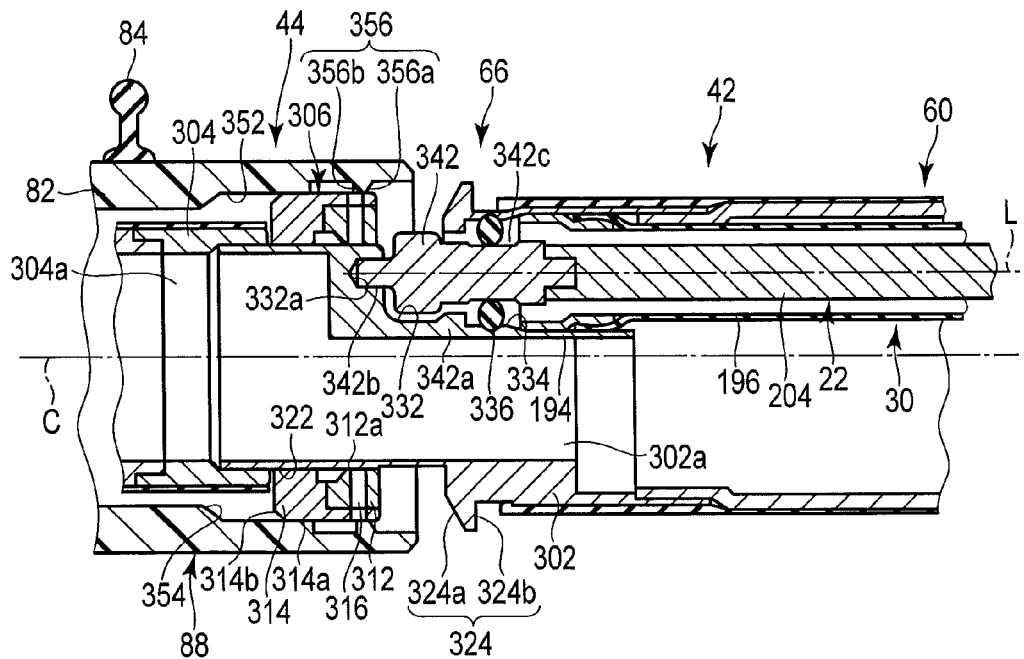
FIG. 11A is a schematic longitudinal sectional view showing how the rotation unit of the insertion portion of the endoscope of the endoscope system according to the second embodiment is moved to the proximal side of the central axis of the insertion unit to attach the rotation unit to the outer circumference of the insertion unit, or showing a state immediately after the rotation unit is removed from the outer circumference of the insertion unit.
Figure 11B:
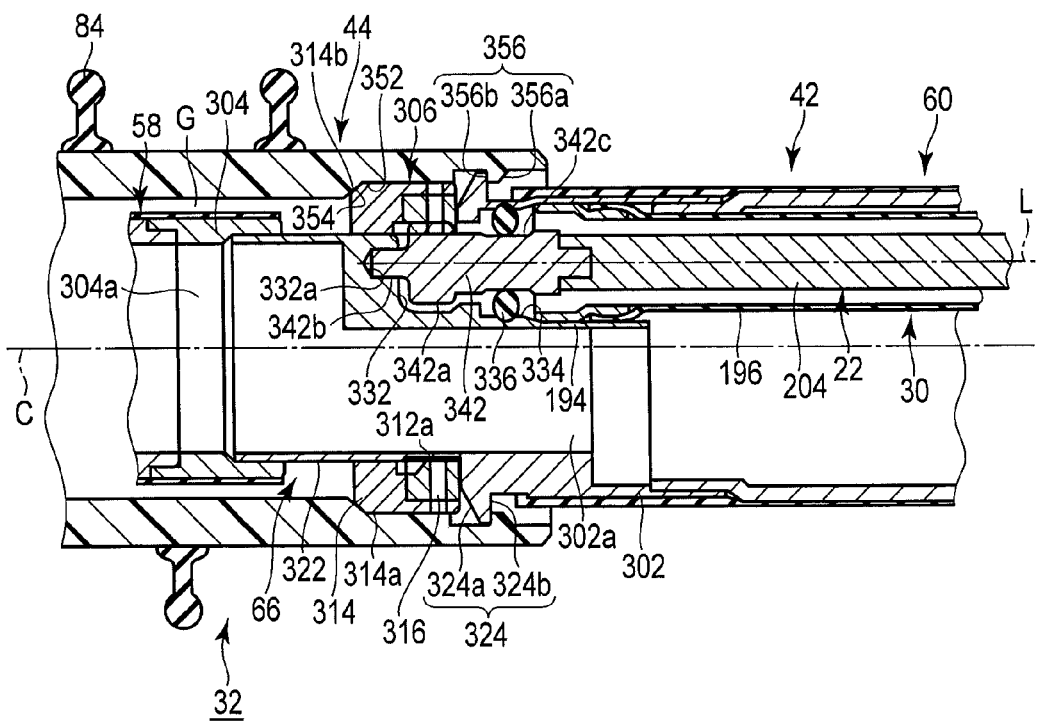
FIG. 11B is a schematic longitudinal sectional view showing how the rotation unit of the insertion portion of the endoscope of the endoscope system according to the second embodiment is attached to the outer circumference of the insertion unit.

Thus, when the rotation unit 44 moves from a position shown in FIG. 11A to a position shown in FIG. 11B, the inclined surface 356a of the diametrically inwardly projecting engagement portion 356 of the tube proximal portion 88 of the rotation unit 44 is elastically deformed together with its peripheral part, and then climbs over the inclined surface 324a of the engagement portion 324 of the connection sleeve 302 of the flexible tube connection portion 66. Thus, the orthogonal plane 356b of the engagement portion 356 of the tube proximal portion 88 of the rotation unit 44 engages with the orthogonal plane 324b of the engagement portion 324 of the connection sleeve 302. Here, both the orthogonal plane 324b on the proximal side of the engagement portion 324 of the connection sleeve 302 and the orthogonal plane 356b on the distal side of the engagement portion 356 of the rotation unit 44 are planes which intersect at right angles with the central axis C, and therefore come into contact. Thus, the tube proximal portion 88 can apply a force that can maintain the engagement with the insertion unit 42 while the engagement portions 324 and 356 are engaged with each other.

The fit surface 352 which has the same shape as the outer circumferential surface 314a of the rotation member 306 and which is fitted to the outer circumferential surface 314a of the rotation member 306 is formed on the inner circumference of the tube proximal portion 88 closer to the proximal side than the engagement portion 356. The outer circumferential surface 314a of the rotation member 306 and the fit surface 352 of the tube proximal portion 88 are formed into, for example, a substantially octagonal shape.

The press portion 354 which projects diametrically inward toward the central axis C as compared with the fit surface 352 is formed on the side of the tube proximal portion 88 closer to the distal side than the fit surface 352. The minimum inside diameter of the press portion 354 is larger than the outside diameter of the first flexible tube 58, and the gap G is provided between the inner circumferential surface of the tube proximal portion 88 and the outer circumferential surface of the first flexible tube 58.

Now, the operation of the endoscope system 10 according to this embodiment is described. Here, an assembly procedure for attaching the rotation force transmission unit 22 and the rotation unit 44 to the insertion unit 42 and attaching the driving source 24 to the operation portion 34 is mainly described.

The rotation force transmission unit 22 according to this embodiment is previously provided in the channel 30 as shown in FIG. 11A. Although not shown, the driving source 24 is also provided in the attachment portion 222. That is, the outer circumferential gear portion 342a of the rotation gear 342 is provided in the gear location cavity 332 of the flexible tube connection portion 66 and exposed to the outside, and the O-ring 336 is provided on the outer circumference of the annular receiving portion 342c, so that it is possible to prevent a liquid from coming into the channel sleeve 194 and the channel tube 196 from the gear location cavity 332 through the O-ring 336.

In this case, since the rotation gear 342 is supported by the O-ring 336 and the depressed support portion 332a at distal end of the gear location cavity 332, the longitudinal axis L of the rotation force transmission unit 22 is parallel with the central axis C of the insertion unit 42.

The rotation unit 44 is then moved toward the proximal end of the insertion unit 42 while being rotated around the central axis C. That is, the engagement portion 356 at the proximal end of the tube proximal portion 88 of the rotation unit 44 is moved toward the proximal side through the outside of the rotation member 306 of the flexible tube connection portion 66. The rotation unit 44 is appropriately rotated in the circumferential direction to bring into the same direction the outer circumferential surface 314a of the rotation member 306 and the fit surface 352 of the tube proximal portion 88 of the rotation unit 44 so that they can fit to each other. The fit surface 352 of the rotation unit 44 is then fitted to the outer circumferential surface 314a of the rotation member 306.

In this condition, the rotation unit 44 located at the position shown in FIG. 11A is relatively moved to the proximal side of the insertion unit 42 up to the position shown in FIG. 11B along the axial direction of the central axis C of the connection sleeve 302. Thus, the contact portion 314b of the rotation member 306 is pressed toward the proximal side by the press portion 354 of the rotation unit 44. The rotation member 306 is moved to the proximal side in the axial direction of the central axis C of the connection sleeve 302 along the slide surface 322.

As shown in FIG. 11B, the internal teeth 312a of the rotation member 306 and the outer circumferential gear portion 342a of the rotation gear 342 mesh with each other, and the engagement portion 356 of the tube proximal portion 88 climbs over the inclined surface 324a of the engagement portion 324 of the flexible tube connection portion 66 of the insertion unit 42 and engages with the orthogonal plane 324b adjacent on the proximal side. That is, the press portion (contact portion) 354 disposes the rotation member 306 on the outer circumference of the rotation gear 342 while the engagement portion 356 is engaged with the outer circumferential surface of the connection sleeve 302.

Thus, the rotation unit 44 is engaged with and fixed to the insertion unit 42.

The insertion portion 32 of the endoscope 12 is available in this state.

After the use of the endoscope 12, the endoscope 12 is washed, disinfected, and sterilized, and then reused. This procedure is briefly described.

The orthogonal plane 356b of the engagement portion 356 of the rotation unit 44 engaging with the orthogonal plane 324b of the engagement portion 324 of the flexible tube connection portion 66 of the insertion unit 42 is elastically deformed to climb over the orthogonal plane 324b of the engagement portion 324 of the flexible tube connection portion 66 so that the engagement portion 356 of the rotation unit 44 is moved closer to the distal side of the insertion unit 42 than the engagement portion 324 of the insertion unit 42. The engagement portion 356 at the proximal end of the tube proximal portion 88 of the rotation unit 44 is then moved toward the distal side through the outside of the rotation member 306 of the flexible tube connection portion 66. Accordingly, the rotation force transmission unit 22 can be removed from the channel 30.

The rotation member 306 is then moved to the distal side of the insertion unit 42 and brought into contact with the proximal end of the distal side sleeve 304. At the same time, the openings 316 of the rotation member 306 are located at the position facing the gear location cavity 332. Thus, when, for example, a washing fluid or a brush is inserted into the channel 30 from the gear location space 192, the region up to the O-ring 336 can be easily washed.

As described above, the following can be said according to this embodiment.

When the rotation unit 44 is attached to the insertion unit 42, no additional components for the attachment are needed. That is, when the rotation unit 44 is attached to the insertion unit 42, the fit surface 352 of the rotation unit 44 is aligned with the direction in which the fit surface 352 can be fitted to the outer circumferential surface 314a of the rotation member 306. The contact portion 314b of the rotation member 306 is then pressed toward the proximal side of the insertion unit 42 by the press portion 354, and the engagement portion 356 of the rotation unit 44 is then engaged with the engagement portion 324 of the connection sleeve 302. As a result, the attachment is completed. Thus, the rotation unit 44 can be easily attached to the insertion unit 42.

When the rotation unit 44 is detached from the insertion unit 42, no additional components for the detachment are needed. That is, when the rotation unit 44 is detached from the insertion unit 42, the engagement portion 356 of the rotation unit 44 is moved to the distal side of the insertion unit 42, and is then disengaged from the engagement portion 324 of the connection sleeve 302, and the rotation unit 44 is moved to the distal side of the insertion unit 42. As a result, the detachment of the rotation unit 44 from the insertion unit 42 is completed. Thus, the rotation unit 44 can be easily detached from the insertion unit 42.

The rotation force transmission unit 22 according to this embodiment is supported by what is known as both-ends-supporting to rotate so that the projecting portion 342b at the distal end of the rotation gear 342 is supported by the support portion 332a and so that the O-ring 336 provided on the outer circumference of the annular receiving portion 342c at the proximal end of the rotation gear 342 is supported at a predetermined position relative to the connection sleeve 302.

Thus, it is possible to effectively prevent the rotation gear 342 from being out of alignment with the longitudinal axis L while being rotated or from moving to the proximal side along the longitudinal axis L.

Now, a first modification of the first and second embodiments is described with reference to FIG. 12A. This embodiment is a modification of the first and second embodiments. The same components as the components described in the first and second embodiments are indicated by the same reference signs and are not described in detail.

In this modification, the modifications of the rotation gear 202 and the collar 206 of the rotation force transmission unit 22 are described.

Figure 12A:
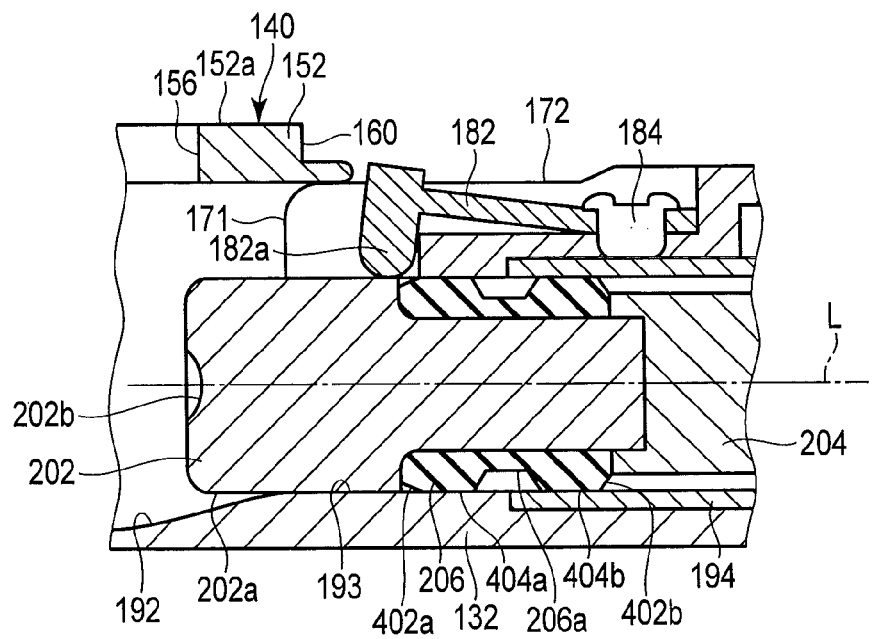
FIG. 12A is a schematic longitudinal sectional view showing how the rotation gear of the rotation force transmission unit (insertion body) is to be disposed in the gear location cavity at the distal end of the channel of the insertion unit of the insertion portion of the endoscope of the endoscope system according to a first modification of the first and second embodiments, and also showing how a protrusion of a leaf spring is pushed aside to greatly elastically deform the leaf spring against a spring energizing force when the maximum diameter of the rotation gear is substantially the same as the maximum diameter of a sliding cylinder.

As shown in FIG. 12A, the depressed groove 206a of the collar 206 is formed, for example, substantially halfway between the distal end and the proximal end. In addition to the depressed groove 206a, the collar 206 has an annular distal side inclined surface (first inclined surface) 402a on the side located close to the external teeth 202a of the rotation gear 202, and an annular proximal side inclined surface 402b on the side located far from the external teeth 202a of the rotation gear 202. Moreover, a distal side slide surface 404a is formed between the depressed groove 206a and the distal side inclined surface 402a, and a proximal side slide surface 404b is formed between the depressed groove 206a and the proximal side inclined surface 402b. The distal side slide surface 404a and the proximal side slide surface 404b are maximum outside diameter portions of the collar 206.

The distal side inclined surface 402a is located on the distal side of the distal side slide surface 404a of the collar 206, and is formed to decrease in outside diameter toward the distal side as compared with the maximum outside diameter. The proximal side inclined surface 402b is located on the proximal side of the proximal side slide surface 404b of the collar 206, and is formed to decrease in outside diameter toward the proximal side as compared with the maximum outside diameter.

The relation between the distal side slide surface 404a and the proximal side slide surface 404b of the collar 206 and the support portion 193 makes it possible to prevent the rotation gear 202 from being out of alignment with the longitudinal axis L while being rotated. The distal side inclined surface 402a and the proximal side inclined surface 402b are formed so that the area of contact of the distal side slide surface 404a and the proximal side slide surface 404b with the support portion 193 can be reduced. Therefore, the collar 206 can be smoothly rotated relative to the support portion 193.

When the areas of the distal side slide surface 404a and the proximal side slide surface 404b of the collar 206 are larger and when the areas of the distal side inclined surface 402a and the proximal side inclined surface 402b are smaller, the rotation of the collar 206 around the longitudinal axis L can be more stable.

When the depth of the depressed groove 206a is greater and when the leaf spring 182 is made less deformable, for example, by selecting materials or by reducing the distance from the screw 184 to the protrusion 182a, the fixing force (engaging force) of the rotation force transmission unit 22 relative to the channel 30 can be greater.

Figure 12B:
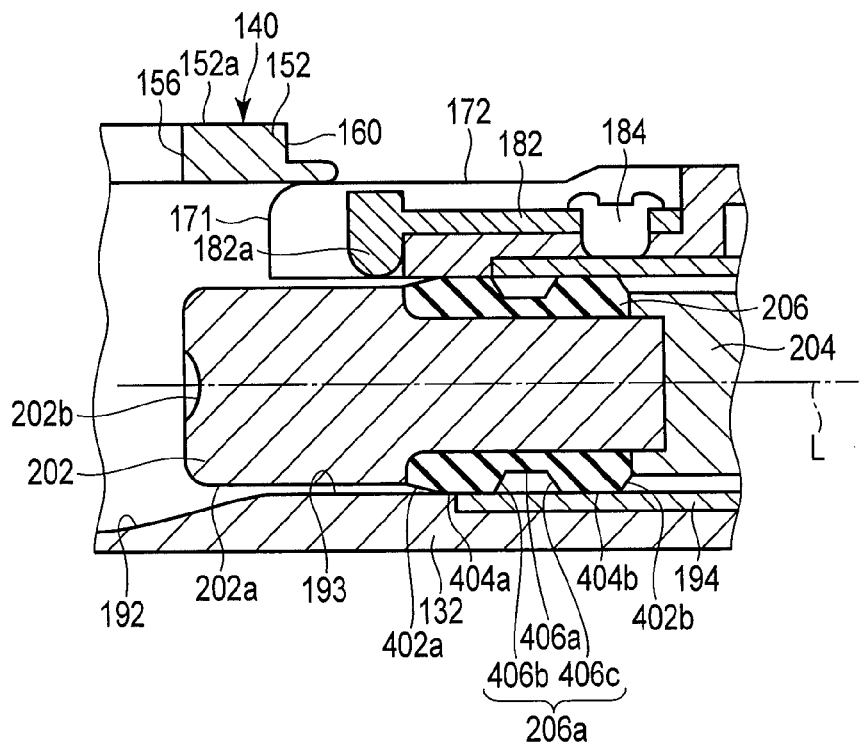
FIG. 12B is a schematic longitudinal sectional view showing how the rotation gear of the rotation force transmission unit (insertion body) is to be disposed in the gear location cavity at the distal end of the channel of the insertion unit of the insertion portion of the endoscope of the endoscope system according to the first modification of the first and second embodiments, and also showing that the maximum diameter of the rotation gear is smaller than the maximum diameter of the sliding cylinder, and the leaf spring is hardly elastically deformed, so that the protrusion of the leaf spring moves along the outer circumferential surface of the rotation gear while being hardly influenced by the spring energizing force.

A further modification of the modification shown in FIG. 12A is shown in FIG. 12B.

As shown in FIG. 12B, the outside diameter of the external teeth 202a of the rotation gear 202 is formed to be smaller than the maximum outside diameter of the collar 206. Thus, when the external teeth 202a of the rotation gear 202 are moved along the protrusion 182a of the leaf spring 182, the deformation amount of the leaf spring 182 can be reduced. It is also possible to maximally prevent the spring urging force of the leaf spring 182 from being applied to the rotation gear 202, between the rotation gear 202 and the collar 206.

In this modification, the outside diameter of the distal end of the distal side inclined surface 402a of the collar 206 is formed to be substantially the same as the outside diameter of the proximal end of the external teeth 202a of the rotation gear 202. Thus, when the external teeth 202a of the rotation gear 202 and the distal side inclined surface 402a of the collar 206 are brought into contact with the protrusion 182a of the leaf spring 182 in this order, it is possible to prevent the protrusion 182a of the leaf spring 182 from being caught in the vicinity of the boundary between the rotation gear 202 and the distal end of the collar 206. That is, the protrusion 182a of the leaf spring 182 can be smoothly moved, without being caught, in the inclined surface 202c and the external teeth 202a of the rotation gear 202, the distal side inclined surface 402a of the collar 206, the distal side slide surface 404a, and the depressed groove 206a in order. Therefore, a person who inserts the rotation force transmission unit 22 through the rotation gear 202 and the drive shaft 204 can easily recognize vibration generated when the depressed groove 206a of the collar 206 engages with the protrusion 182a of the leaf spring 182.

In this modification, the depressed groove 206a has a bottom surface 406a, an annular distal side continuous inclined surface (second inclined surface) 406b formed continuously with the distal side of the bottom surface 406a, and a proximal side continuous inclined surface 406c formed continuously with the proximal side of the bottom surface 406a.

Here, the inclination angle of the distal side inclined surface 402a with the longitudinal axis L is smaller than the inclination angle of the distal side continuous inclined surface 406b of the depressed groove 206a. That is, the inclination angle of the distal side inclined surface 402a with the longitudinal axis L is gentler than the inclination angle of the distal side continuous inclined surface 406b of the depressed groove 206a. In other words, the inclination angle of the distal side continuous inclined surface 406b of the depressed groove 206a is sharper than the inclination angle of the distal side inclined surface 402a with the longitudinal axis L. Thus, when the depressed groove 206a of the collar 206 is engaged with the protrusion 182a of the leaf spring 182, that is, when the protrusion 182a of the leaf spring 182 climbs over the distal side inclined surface 402a of the collar 206 and engages with the depressed groove 206a, the protrusion 182a of the leaf spring 182 smoothly moves without being caught. On the other hand, when the depressed groove 206a of the collar 206 is disengaged from the protrusion 182a of the leaf spring 182, that is, when the protrusion 182a of the leaf spring 182 climbs over the distal side continuous inclined surface 406b of the depressed groove 206a of the collar 206 and is located on the distal side slide surface 404a or the distal side inclined surface 402a, the amount of force to pull the drive shaft 204 needs to be greater. That is, it is possible to prevent the rotation force transmission unit 22 from moving to the proximal side against the urging force of the leaf spring 182 during the use of the endoscope 12.

The distal side inclined surface 402a, the proximal side inclined surface 402b, the distal side continuous inclined surface 406b, and the proximal side continuous inclined surface 406c of the collar 206 are preferably formed into tapered shapes each having a given inclination angle.

Now, a second modification is described with reference to FIG. 13A and FIG. 13B. This modification is not only a modification of the first and second embodiments but also a further modification of the first modification. The same components as the components described in the first and second embodiments and in the first modification are indicated by the same reference signs and are not described in detail.

Figure 13A:
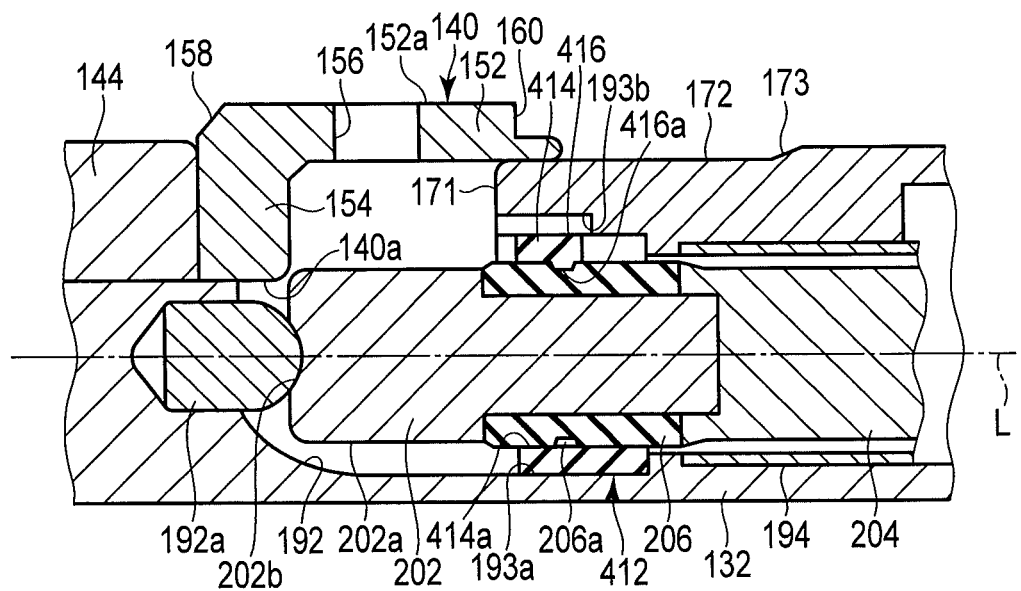
FIG. 13A is a schematic longitudinal sectional view showing how the rotation gear of the rotation force transmission unit (insertion body) is disposed in the gear location cavity at the distal end of the channel of the insertion unit of the insertion portion of the endoscope of the endoscope system according to a second modification of the first and second embodiments and how a cylindrical spring protrusion is fitted in a depressed groove of the sliding cylinder.
Figure 13B:
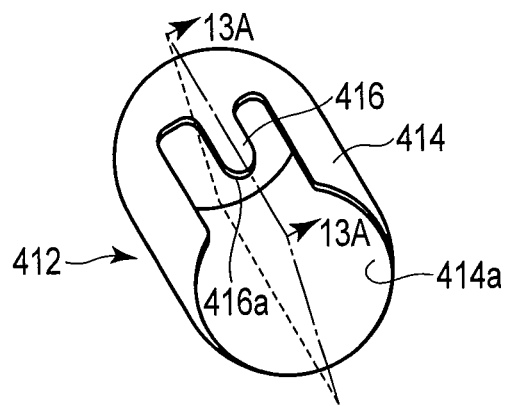
FIG. 13B is a schematic perspective view showing a cylindrical member provided on the outer circumference of a slide member.

As shown in FIG. 13A, in this modification, a cylindrical member 412 shown in FIG. 13B is fixed to the connection sleeve 132 instead of the leaf spring 182. As shown in FIG. 13A, the connection sleeve 132 has an annular depression 193a at a position continuous with the gear location cavity 192. The cylindrical member 412 is provided in and fixed to the annular depression 193a.

A depressed groove (depressed portion) 193b which permits the elastic deformation of a later-described engagement portion (elastic press member) 416 is formed in the annular depression 193a. That is, the depressed groove 193b of the connection sleeve 132 forms a depressed portion into which the engagement portion 416 escapes.

As shown in FIG. 13A and FIG. 13B, the cylindrical member 412 has a cylindrical portion 414, and the engagement portion 416 integrated with the cylindrical portion 414. The engagement portion 416 has a projecting portion (protruding portion) 416a as an elastic press member which projects inwardly in the diametrical direction of the cylindrical portion 414. The projecting portion (insertion apparatus side engagement portion) 416a is preferably formed in the same manner as the protrusion 182a of the leaf spring 182 described above. An inner circumferential surface 414a of the cylindrical portion 414 functions in the same manner as the support portion 193 described in the first and second embodiments. The engagement portion 416 serves in the same manner as the leaf spring 182 described in the first and second embodiments.

Thus, as has been described in the first and second embodiments, the projecting portion 416a of the engagement portion 416 of the cylindrical member 412 can detachably engage with the depressed groove 206a of the collar 206.

Although the engagement portion 416 in FIG. 13B is formed to be shorter than the entire length of the cylindrical portion 414 as shown in FIG. 13A, the spring strength can be easily adjusted by adjusting the length of the engagement portion 416. That is, it is possible to easily adjust the engaging force (fixing force) of the projecting portion 416a of the engagement portion 416 of the cylindrical member 412 relative to the depressed groove 206a of the collar 206.

Although the engagement portion 416 is disposed to extend in a direction from the distal side to the proximal side in FIG. 13A, the engagement portion 416 may be formed to extend in the opposite direction, that is, to extend in a direction from the proximal side to the distal side.

Now, a third modification is described with reference to FIG. 14. This modification is not only a modification of the first and second embodiments but also a further modification of the first and second modifications. The same components as the components described in the first and second embodiments and in the first and second modifications are indicated by the same reference signs and are not described in detail.

In this modification, the protrusion 182a of the leaf spring 182, that is, the protruding portion, and the depressed groove 206a of the collar 206, that is, the depressed portion are reversed.

Figure 14:
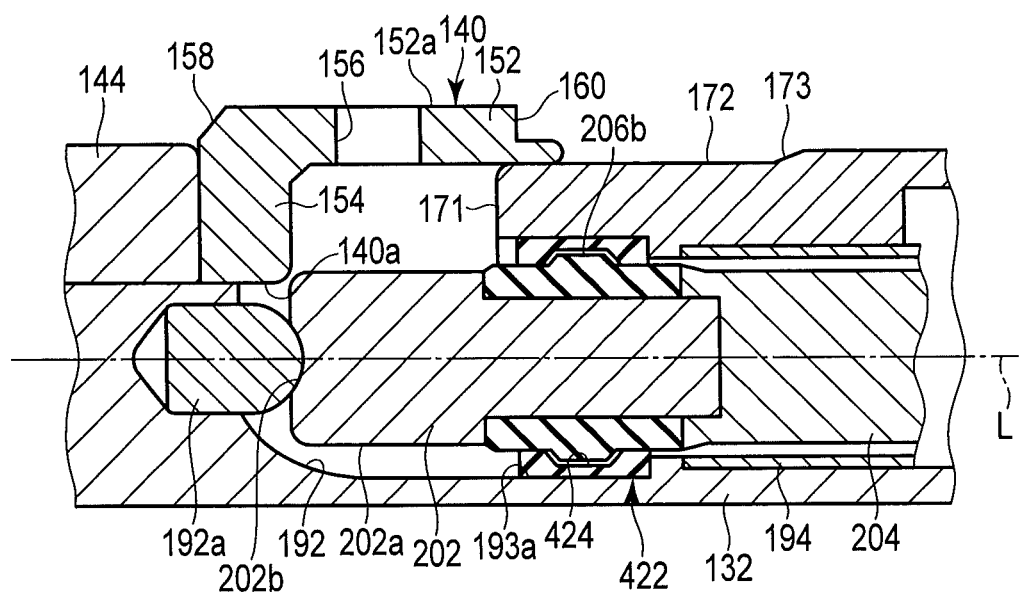
FIG. 14 is a schematic longitudinal sectional view showing how the rotation gear of the rotation force transmission unit (insertion body) is disposed in the gear location cavity at the distal end of the channel of the insertion unit of the insertion portion of the endoscope of the endoscope system according to a third modification of the first and second embodiments and how an annular depression is fitted to a discrete or annular protrusion of the sliding cylinder.

As shown in FIG. 14, in this modification, a cylindrical member 422 is fixed to the connection sleeve 132 instead of the leaf spring 182. That is, as shown in FIG. 14, the connection sleeve 132 has the annular depression 193a at the position continuous with the gear location cavity 192. The cylindrical member 422 is provided in and fixed to the annular depression 193a.

The cylindrical member 422 has, on its inner circumferential surface, an annular depressed groove (insertion apparatus side engagement portion) 424.

The collar 206 has no depressed groove 206a, and has a protruding portion 206b which engages with the annular depressed groove 424 of the cylindrical member 422. More than one protruding portion 206b may be discretely formed, or the protruding portion 206b may be annularly formed. The outside diameter of the collar 206 including the protruding portion 206b is formed to be slightly smaller than the inside diameter of the channel sleeve 194 of the channel 30 and the inside diameter of the channel tube 196. On the other hand, the inside diameter of the proximal end of the cylindrical member 422 is formed to be smaller than the inside diameter of the channel sleeve 194. Thus, when the protruding portion 206b of the collar 206 is engaged with the depressed groove 424 of the cylindrical member 422, the protruding portion 206b of the collar 206 or the cylindrical member 422 is elastically deformed to engage the protruding portion 206b of the collar 206 with the depressed groove 424 of the cylindrical member 422.

In this configuration as well, the endoscope system 10 can be used in the same manner as the endoscope system 10 described in the first embodiment.

Now, a fourth modification is described with reference to FIG. 15 and FIG. 16. This modification is not only a modification of the first and second embodiments but also a further modification of the first to third modifications. The same components as the components described in the first and second embodiments and in the first to third modifications are indicated by the same reference signs and are not described in detail.

Figure 15:
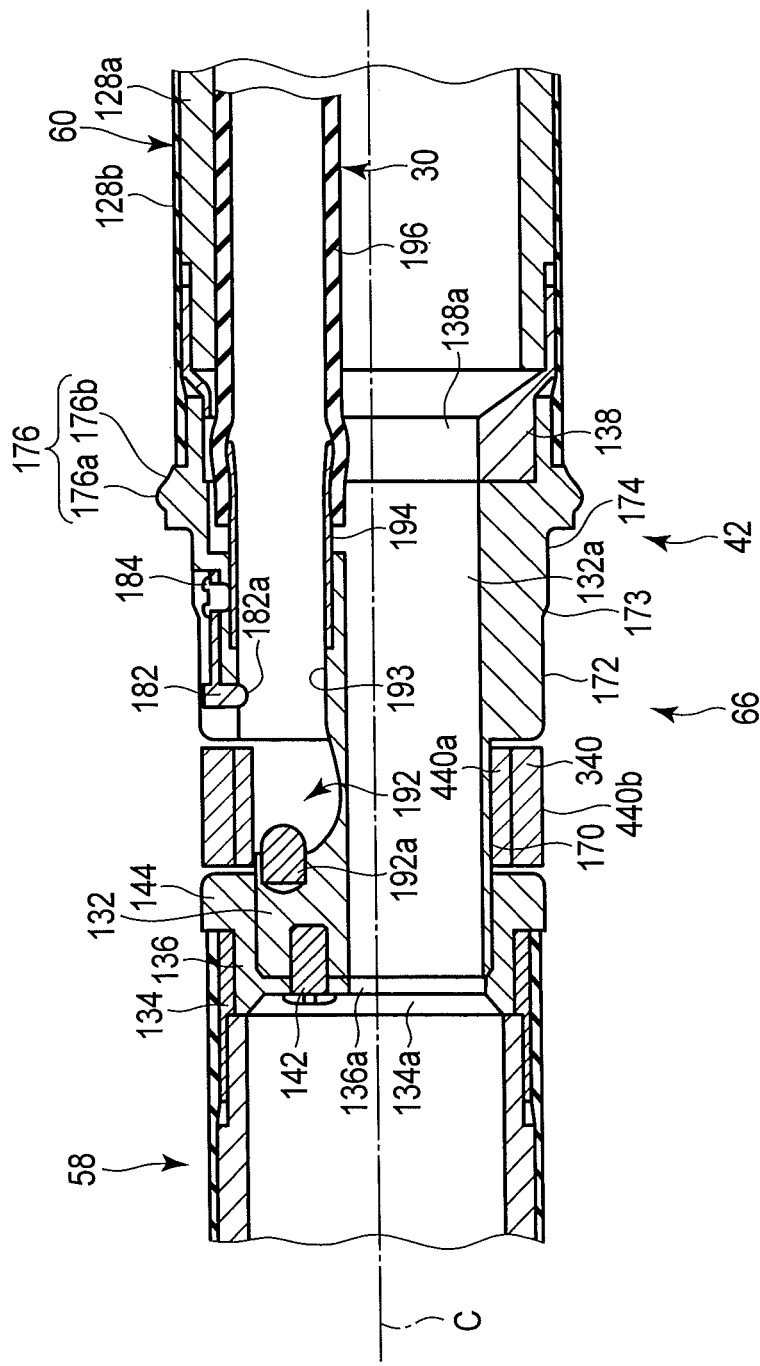
FIG. 15 is a schematic longitudinal sectional view showing the flexible tube connection portion between the first flexible tube and the second flexible tube in the insertion portion of the endoscope of the endoscope system according to a fourth modification of the first and second embodiments.

In the flexible tube connection portion 66 of the insertion unit 42 shown in FIG. 15, another rotation member 440 is used instead of the rotation member 140 described in the first embodiment. This rotation member 440 has internal teeth 440a. The flexible tube connection portion 66 shown in FIG. 15 does not have the coil spring (energizing portion) 180 described in the first embodiment. An outer circumferential surface 440b of the rotation member 440 is formed into a regular polygon such as an equilateral octagonal shape that is fitted to the inner circumferential surface of the rotation unit 44, in the same manner as the outer circumferential surface 152a of the rotation member 140 described in the first embodiment.

Instead of the fit surface 266 described in the first embodiment, another fit surface 446 is formed on the inner circumferential surface of the inner cylindrical portion 252 of the rotation unit 44 shown in FIG. 16. The outer circumferential surface 440b of the rotation member 440 according to this embodiment is fitted to the fit surface 446. Instead of the press portion 268 described in the first embodiment, a circumferential surface (depressed portion) 448 is formed on the inner circumferential surface of the inner cylindrical portion 252 of the rotation unit 44 shown in FIG. 16. This circumferential surface 448 is formed to rotatably cover the outer circumferential surface of the large-diameter circumferential surface 172 of the connection sleeve 132. Thus, it is possible to inhibit the elastic deformation of the leaf spring 182 while the rotation unit 44 is attached to the insertion unit 42. That is, it is possible to prevent the rotation force transmission unit 22 from unintentionally moving to the proximal side of the channel 30 during the use of the endoscope 12.

The fit surface 446 and the circumferential surface 448 are continuously formed adjacent to each other.

Even when the flexible tube connection portion 66 of the insertion unit 42 is formed in this way, it is possible to attach and detach the rotation force transmission unit 22 to and from the insertion unit 42 through the channel 30 as described in the first embodiment.

The circumferential surface 448 of the insertion unit 42 functions as an assist portion which can assist the protrusion 182a of the leaf spring 182 in maintaining engagement with the depressed groove 206a of the collar 206. Thus, when the rotation force transmission unit 22 is rotating and the rotation member 440 is rotating accordingly, the movement of the rotation force transmission unit 22 in the axial direction of the longitudinal axis L is prevented.

Now, a fifth modification is described with reference to FIG. 17. This modification is not only a modification of the first and second embodiments but also a further modification of the first to fourth modifications. The same components as the components described in the first and second embodiments and in the first to fourth modifications are indicated by the same reference signs and are not described in detail.

Figure 17:
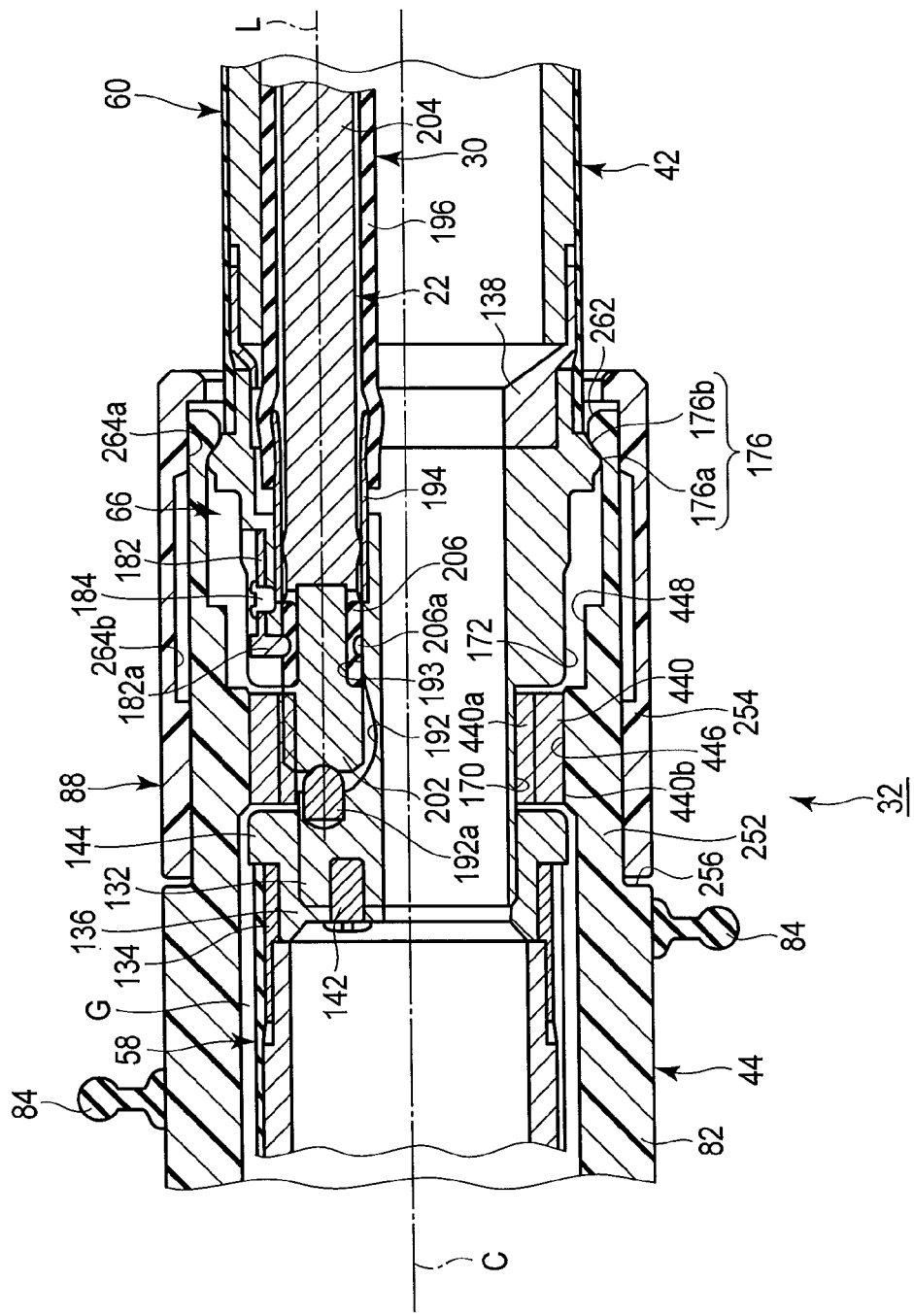
FIG. 17 is a schematic longitudinal sectional view showing how the rotation unit of the insertion portion of the endoscope of the endoscope system according to a fifth modification of the first and second embodiments is attached to the outer circumference of the insertion unit.

As shown in FIG. 17, the distance between the screw 184 for fixing the leaf spring 182 and the protrusion 182a of the leaf spring 182 according to this modification is formed to be smaller than the distance between the screw 184 and the protrusion 182a of the leaf spring 182 according to the fourth modification. If the material and thickness of the leaf spring 182 are the same, the leaf spring 182 according to this modification is more difficult to elastically deform. Thus, the inside diameter of the circumferential surface 448 described in the fourth modification can be increased. That is, a gap which permits the elastic deformation of the leaf spring 182 may be formed between the large-diameter circumferential surface 172 on the outer circumferential surface of the connection sleeve 132 and the circumferential surface 448 of the inner cylindrical portion 252 of the rotation unit 44. Thus, it is possible to keep the rotation force transmission unit 22 held in the channel 30. For example, in an emergency, the rotation force transmission unit 22 can be removed from the channel 30 only by strongly pulling the rotation force transmission unit 22.

Although the rotation unit 44 is attached to the insertion unit 42 of the endoscope 12 in the examples described above according to the embodiments including the modifications, this invention is not limited to the endoscope 12. For example, it is possible to use a structure that permits the rotation unit 44 to be attached to and detached from the insertion unit 42 of, for example, a surgical manipulator (insertion apparatus).

[Additional Statement]
[Additional Item 1]

An insertion body which is attachable to and detachable from a channel of an insertion apparatus and which is configured to transmit a rotational force to a cylindrical rotation unit via a rotation member while being provided in the channel, the insertion apparatus including an elongated insertion unit in which a central axis is defined and which is rotatable around the central axis and which has the rotation member having internal teeth, the rotation unit provided rotatably relative to the insertion unit in accordance with the rotation of the rotation member, and the channel which is provided along a longitudinal axis defined at a position out of alignment with the central axis of the insertion unit and which is in communication with the internal teeth of the rotation member, the insertion body comprising:

a rotation gear which is rotatable around the longitudinal axis in the channel and which has external teeth configured to mesh with the internal teeth of the rotation member;

a drive shaft which extends toward a proximal side from the proximal end of the rotation gear along the longitudinal axis and which is configured to rotate the rotation gear when the rotation force around the longitudinal axis is applied to the proximal end of the drive shaft; and a rotating cylinder which is provided on the outer circumferential surface of at least one of the rotation gear and the drive shaft and which has an insertion body side engagement portion engageable with the insertion apparatus, the rotation of the rotating cylinder around the longitudinal axis being permitted and the movement of the rotating cylinder in the axial direction of the longitudinal axis being regulated while the insertion body side engagement portion is engaged with the insertion apparatus.

[Additional Item 2]
The insertion body according to additional item 1, wherein the maximum outside diameter of the rotating cylinder is larger than the maximum outside diameter of the external teeth of the rotation gear.

[Additional Item 3]
The insertion body according to additional item 1, wherein the insertion apparatus has a protruding portion which is provided in the insertion unit and which projects into the channel, the insertion body side engagement portion of the rotating cylinder has, on the outer circumferential surface of the rotating cylinder, an annular depression engageable with the protruding portion, a first inclined surface is annularly formed on the outer circumferential surface of the distal end of the rotating cylinder, a second inclined surface is annularly formed on the side of the depression close to the distal end of the rotation gear, and the first inclined surface is formed more gently than the second inclined surface.

[Additional Item 4]
The insertion body according to additional item 1, wherein the diameter of the distal end of the outer circumferential surface of the rotating cylinder is the same as the diameter of the proximal end of the external teeth of the rotation gear or is smaller than the diameter of the proximal end of the external teeth of the rotation gear, and a maximum diameter between the distal end of the outer circumferential surface of the rotating cylinder and the insertion apparatus side engagement portion is larger than the outside diameter of the proximal end of the external teeth of the rotation gear.

[Additional Item 5]
The insertion body according to additional item 1, wherein the insertion body side engagement portion is formed to be disengageable from the insertion apparatus in the case where the drive shaft is moved to the proximal side of the channel along the longitudinal axis of the channel when the rotation unit rotates in accordance with the rotation of the rotation member.

[Additional Item 6]
An insertion apparatus in which the insertion body according to additional item 1 is provided, the insertion apparatus comprising:

an elongated insertion unit in which a central axis is defined and which is rotatable around the central axis and which has a rotation member having internal teeth;

a cylindrical rotation unit provided rotatably relative to the insertion unit in accordance with the rotation of the rotation member;

a channel which is provided along a longitudinal axis defined at a position out of alignment with the central axis of the insertion unit and which is in communication with the internal teeth of the rotation member; and an insertion apparatus side engagement portion engageable with the insertion body side engagement portion of the rotating cylinder.

[Additional Item 7]

The insertion apparatus according to additional item 5, wherein the insertion apparatus side engagement portion has an elastic press member which presses the rotating cylinder of the insertion body.

[Additional Item 8]

The insertion apparatus according to additional item 6, wherein the insertion unit has an assist portion which is configured to assist the insertion apparatus side engagement portion in keeping engaged with the insertion body side engagement portion.

[Additional Item 9]

The insertion apparatus according to additional item 6, wherein the insertion unit has a depressed portion into which the insertion apparatus side engagement portion escapes.

[Additional Item 10]

The insertion apparatus according to additional item 6, wherein the insertion apparatus side engagement portion is disengageable from the insertion body side engagement portion in the case where the drive shaft is moved to the proximal side of the channel along the longitudinal axis of the channel.

[Additional Item 11]

An insertion system comprising:
the insertion body according to additional item 1; and
the insertion apparatus according to additional item 6.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cylindrical rotation unit rotatably driven relative to an elongated insertion unit when the rotation unit moves relative to the elongated insertion unit in an axial direction of a central axis of the elongated insertion unit, the elongated insertion unit including a base in which the central axis is defined, and a rotation member provided on an outer circumference of the base movably in the central axis relative to the base and rotatably around the central axis in response to the rotation of a rotation force transmission portion which is rotatable around a longitudinal axis parallel with the central axis of the base, the rotation unit comprising:
    an engagement portion attachable to and detachable from an outer circumferential surface of the base; and
    a contact portion which is provided to contact on the rotation member away from the engagement portion and which disposes the rotation member on an outer circumference of the rotation force transmission portion while the engagement portion is engaged with the outer circumferential surface of the base.

2. The rotation unit according to claim 1, further comprising a cylindrical portion which has the engagement portion and the contact portion and which is disposed outside the base of the elongated insertion unit and which is rotatable around the central axis and movable in the axial direction of the central axis.

3. The rotation unit according to claim 1, wherein the contact portion is configured to move the rotation member to the proximal side of the elongated insertion unit against energizing by an energizing portion which energizes the base to separate the rotation member toward the distal side of the elongated insertion unit along the central axis, and
    the engagement portion is engageable with the outer circumferential surface of the base against the energizing of the energizing portion of the base.

4. The rotation unit according to claim 1, further comprising, on its inner circumferential surface, a fit portion which fits to the outer circumferential surface of the rotation member so that a rotational force around the central axis of the rotation member having an outer circumferential portion formed into a polygonal shape is transmitted.

5. The rotation unit according to claim 1, further comprising, on its outer circumference, a spiral fin portion.

6. An insertion apparatus comprising:
    the rotation unit according to claim 1; and
    the elongated insertion unit being rotatably driven relative to the rotation unit when the rotation unit moves relative to the elongated insertion unit in the axial direction of the central axis of the elongated insertion unit, the elongated insertion unit including a base in which the central axis is defined, and a rotation member provided on an outer circumference of the base movably in the central axis relative to the base and rotatably around the central axis in response to the rotation of a rotation force transmission portion which is rotatable around a longitudinal axis parallel with the central axis of the base.

7. The insertion apparatus according to claim 6, wherein the engagement portion is formed into a protruding portion attachable to and detachable from the outer circumferential surface of the base, and
    the outer circumferential surface of the base with which the engagement portion is engageable has at least one of a protruding portion and a depressed portion to be engaged with the protruding portion of the engagement portion.

8. The insertion apparatus according to claim 6, wherein the elongated insertion unit further has a channel through which a rotation force transmission unit having the rotation force transmission portion is inserted, and
    the rotation member has an opening which is in communication with the channel and which allows a washing material to be put in and out.

9. The insertion apparatus according to claim 6, wherein the base of the elongated insertion unit has an energizing portion which energizes the rotation member to separate toward the distal side of the elongated insertion unit along the central axis,
    the contact portion of the rotation unit is configured to move the rotation member to the proximal side of the elongated insertion unit against an energizing force of the energizing portion, and
    the engagement portion of the rotation unit is engageable with the outer circumferential surface of the base against the energizing force of the energizing portion of the base.

10. The insertion apparatus according to claim 6, wherein the rotation member has, on its outer circumference, an outer circumferential portion formed into a polygonal shape, and
    the rotation unit has, on its inner circumferential surface, a fit portion which fits to the outer circumferential surface of the rotation member so that a rotational force of the central axis of the rotation member is transmitted.

11. An insertion body which is attachable to and detachable from a channel of an insertion apparatus and which is configured to transmit a rotational force to a rotation unit according to claim 1 via a rotation member while being provided in the channel, the insertion apparatus including an elongated insertion unit in which a central axis is defined and which is rotatable around the central axis and which has the rotation member having internal teeth, the rotation unit provided rotatably relative to the elongated insertion unit in accordance with the rotation of the rotation member, and the channel which is provided along a longitudinal axis defined at a position out of alignment with the central axis of the elongated insertion unit and which is in communication with the internal teeth of the rotation member, the insertion body comprising:
- a rotation gear which is rotatable around the longitudinal axis in the channel and which has, on the outer circumference, external teeth configured to mesh with the internal teeth of the rotation member;
- a drive shaft which extends toward a proximal side from the proximal end of the rotation gear along the longitudinal axis and which is configured to rotate the rotation gear when the rotation force around the longitudinal axis is applied to the proximal end of the drive shaft; and
- a rotating cylinder which is provided on the outer circumferential surface of at least one of the rotation gear and the drive shaft and which has an insertion body side engagement portion engageable with the insertion apparatus, the rotation of the rotating cylinder around the longitudinal axis being permitted and the movement of the rotating cylinder in the longitudinal axis of a distal end side and a proximal end side being regulated while the insertion body side engagement portion is engaged with the insertion apparatus.

12. The insertion body according to claim 11, wherein the maximum outside diameter of the rotating cylinder is larger than the maximum outside diameter of the external teeth of the rotation gear.

13. The insertion body according to claim 11, wherein the insertion apparatus has a protruding portion which is provided in the elongated insertion unit and which is configured to project into the channel,
- the insertion body side engagement portion of the rotating cylinder has, on the outer circumferential surface of the rotating cylinder, an annular depression engageable with the protruding portion,
- a first inclined surface is annularly formed on the outer circumferential surface of the distal end of the rotating cylinder,
- a second inclined surface is annularly formed on the side of the depression close to the distal end of the rotation gear, and
- the first inclined surface is formed more gently than the second inclined surface.

14. The insertion body according to claim 11, wherein the diameter of the distal end of the outer circumferential surface of the rotating cylinder is the same as the diameter of the proximal end of the external teeth of the rotation gear or is smaller than the diameter of the proximal end of the external teeth of the rotation gear, and
- a maximum diameter between the distal end of the outer circumferential surface of the rotating cylinder and the insertion apparatus side engagement portion is larger than the outside diameter of the proximal end of the external teeth of the rotation gear.

15. The insertion body according to claim 11, wherein the insertion body side engagement portion is formed to be disengageable from the insertion apparatus in the case where the drive shaft is moved to the proximal side of the channel along the longitudinal axis of the channel when the rotation unit rotates in accordance with the rotation of the rotation member.

16. An insertion apparatus comprising:
- the rotation unit according to claim 1, the rotation unit being rotatably driven relative to the elongated insertion unit when the rotation unit moves relative to the elongated insertion unit in the axial direction of the central axis of the elongated insertion unit and provided rotatably relative to the elongated insertion unit in accordance with the rotation of the rotation member;
- an insertion body which is attachable to and detachable from a channel of an insertion apparatus and which is configured to transmit a rotational force to the rotation unit via a rotation member while being provided in the channel, the insertion apparatus including the elongated insertion unit in which the central axis is defined and which is rotatable around the central axis and which has the rotation member having internal teeth, the rotation unit provided rotatably relative to the elongated insertion unit in accordance with the rotation of the rotation member, and the channel which is provided along a longitudinal axis defined at a position out of alignment with the central axis of the elongated insertion unit and which is in communication with the internal teeth of the rotation member, the insertion body comprising:
- a rotation gear which is rotatable around the longitudinal axis in the channel and which has, on the outer circumference, external teeth configured to mesh with the internal teeth of the rotation member;
- a drive shaft which extends toward a proximal side from the proximal end of the rotation gear along the longitudinal axis and which is configured to rotate the rotation gear when the rotation force around the longitudinal axis is applied to the proximal end of the drive shaft; and
- a rotating cylinder which is provided on the outer circumferential surface of at least one of the rotation gear and the drive shaft and which has an insertion body side engagement portion engageable with the insertion apparatus, the rotation of the rotating cylinder around the longitudinal axis being permitted and the movement of the rotating cylinder in the axial direction of the longitudinal axis being regulated while the insertion body side engagement portion is engaged with the insertion apparatus;
- the elongated insertion unit in which the central axis is defined and which is rotatable around the central axis and which has a rotation member having internal teeth;
- a channel which is provided along a longitudinal axis defined at a position out of alignment with the central axis of the elongated insertion unit and which is in communication with the internal teeth of the rotation member; and
- an insertion apparatus side engagement portion engageable with the insertion body side engagement portion of the rotating cylinder.

17. The insertion apparatus according to claim 16, wherein the insertion apparatus side engagement portion has an elastic press member which presses the rotating cylinder of the insertion body.

18. The insertion apparatus according to claim 16, wherein the elongated insertion unit has an assist portion which is configured to assist the insertion apparatus side engagement portion in keeping engaged with the insertion body side engagement portion.

19. The insertion apparatus according to claim 16, wherein the elongated insertion unit has a depressed portion into which the insertion apparatus side engagement portion escapes.

20. The insertion apparatus according to claim 16, wherein the insertion apparatus side engagement portion is disengageable from the insertion body side engagement portion in the case where the drive shaft is moved to the proximal side of the channel along the longitudinal axis of the channel.

* * * * *